US011306072B2

(12) United States Patent
Jove et al.

(10) Patent No.: US 11,306,072 B2
(45) Date of Patent: Apr. 19, 2022

(54) 5-BROMO-INDIRUBINS

(71) Applicants: City of Hope, Duarte, CA (US); National and Kapodistrian University of Athens, Athens (GR)

(72) Inventors: Richard Jove, Pasadena, CA (US); Sangkil Nam, Tujunga, CA (US); David Horne, Altadena, CA (US); Jun Xie, Duarte, CA (US); Alexios Leandros Skaltsounis, Athens (GR); Marina Kritsanida, Athens (GR); Nicolas Gaboriaud-Kolar, Athens (GR)

(73) Assignees: City of Hope, Duarte, CA (US); National and Kapodistrian University of Athens, Athens (GR)

( * ) Notice: Subject to any disclaimer, the term of this patent is extended or adjusted under 35 U.S.C. 154(b) by 0 days.

(21) Appl. No.: 16/790,611

(22) Filed: Feb. 13, 2020

(65) Prior Publication Data

US 2020/0283421 A1 Sep. 10, 2020

Related U.S. Application Data

(63) Continuation of application No. 15/898,151, filed on Feb. 15, 2018, now abandoned, which is a continuation of application No. 14/850,579, filed on Sep. 10, 2015, now abandoned, which is a continuation of application No. PCT/US2014/028730, filed on Mar. 14, 2014.

(60) Provisional application No. 61/783,290, filed on Mar. 14, 2013.

(51) Int. Cl.
| | |
|---|---|
| *C07D 403/14* | (2006.01) |
| *C07D 401/04* | (2006.01) |
| *C07D 209/40* | (2006.01) |
| *C07D 209/48* | (2006.01) |
| *A61K 45/06* | (2006.01) |
| *A61K 31/404* | (2006.01) |
| *A61K 31/4439* | (2006.01) |
| *A61K 31/496* | (2006.01) |
| *C07D 401/14* | (2006.01) |

(52) U.S. Cl.
CPC .......... *C07D 403/14* (2013.01); *A61K 31/404* (2013.01); *A61K 31/4439* (2013.01); *A61K 31/496* (2013.01); *A61K 45/06* (2013.01); *C07D 209/40* (2013.01); *C07D 209/48* (2013.01); *C07D 401/04* (2013.01); *C07D 401/14* (2013.01)

(58) Field of Classification Search
CPC . C07D 403/14; A61K 31/404; A61K 31/4439
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 2006/0078494 A1* | 4/2006 | Polvino | A61K 31/4172 424/1.11 |
| 2008/0227640 A1 | 9/2008 | Bastiaans et al. | |
| 2010/0331327 A1* | 12/2010 | Meijer | A61P 35/00 514/235.2 |
| 2011/0136808 A1 | 6/2011 | Meijer et al. | |
| 2015/0259288 A1 | 9/2015 | Nam et al. | |
| 2016/0068517 A1 | 3/2016 | Jove et al. | |
| 2018/0170870 A1 | 6/2018 | Nam et al. | |
| 2018/0170915 A1 | 6/2018 | Jove et al. | |
| 2020/0247750 A1* | 8/2020 | Nam | C07D 401/14 |

FOREIGN PATENT DOCUMENTS

| | | |
|---|---|---|
| EP | 2 149 553 A1 | 2/2010 |
| EP | 2 149 553 B1 | 2/2010 |
| EP | 2 518-139 A1 | 10/2012 |
| EP | 2 733 140 A1 | 5/2014 |
| JP | 2007-522114 A | 8/2007 |
| WO | WO-01/37819 A2 | 5/2001 |
| WO | WO-01/37819 A3 | 5/2001 |
| WO | WO-2005/069933 A2 | 8/2005 |
| WO | WO-2005/069933 A3 | 8/2005 |
| WO | WO-2005/107466 A1 | 11/2005 |
| WO | WO-2007/099402 A2 | 9/2007 |
| WO | WO-2007/099402 A3 | 9/2007 |
| WO | WO-2010/013168 A1 | 2/2010 |
| WO | WO-2013/011841 A1 | 1/2013 |
| WO | WO-2014/153023 A1 | 9/2014 |

OTHER PUBLICATIONS

Al-Muhammed, J. et al. (May-Jun. 1996). "In-vivo studies on dexamethasone sodium phosphate liposomes," *J Microencapsul* 13(3):293-306.
Bagrintseva, K. et al. (Mar. 15, 2004, e-published Nov. 6, 2003). "Mutations in the tyrosine kinase domain of FLT3 define a new molecular mechanism of acquired drug resistance to PTK inhibitors in FLT3-ITD-transformed hematopoietic cells," *Blood* 103(6):2266-2275.
Beauchard, A. et al. (2006). "Synthesis of novel 5-substituted indirubins as prote in kinase inhibitors," Bioorganic & Medicinal Chemistry 14(18):6434-6443.
Berge, S.M. et al. (Jan. 1977). "Pharmaceutical salts" *J Pharm Sci* 66(1)1-19.
Choi, S.J. et al. (Mar. 15, 2010, e-published Jan. 20, 2010). "Indirubin derivatives as potent FLT3 inhibitors with anti-proliferative activity of acute myeloid leukemic cells," *Bioorg Med Chem Lett* 20(6):2033-2037.
Chonn, A. et al. (Dec. 1995). "Recent advances in liposomal drug-delivery systems," *Curr Opin Biotechnol* 6(6):698-708.
Deininger, M.W. et al. (Nov. 15, 2000). "The molecular biology of chronic myeloid leukemia," *Blood* 96(10):3343-3356.

(Continued)

*Primary Examiner* — Pancham Bakshi
(74) *Attorney, Agent, or Firm* — Wilson Sonsini Goodrich & Rosati

(57) ABSTRACT

Disclosed herein inter alia are compositions and methods for treating cancer using 5-Br-indirubin derivatives.

3 Claims, 12 Drawing Sheets

(56) References Cited

OTHER PUBLICATIONS

Eyles, J.E. et al. (Jul. 1997). "Oral delivery and fate of poly(lactic acid) microsphere-encapsulated interferon in rats," *J Pharm Pharmacol* 49(7):669-674.

Gao, Z.H. et al. (Jun. 1995). "Controlled release of a contraceptive steroid from biodegradable and injectable gel formulations: in vitro evaluation," *Pharm Res* 12(6):857-863.

Ginzinger, W. et al. (Oct. 2012). "Water-Soluble Cationic Derivatives of Indirubin, the Active Anticancer Component from *Indigo naturalis*," *Chemistry & Biodiversity* 9(10):2175-2185.

Goldman, J.M. et al. (Oct. 9, 2003). "Chronic myeloid leukemia—advances in biology and new approaches to treatment," *N Engl J Med* 349(15):1451-1464.

Griffith, J. et al. (Jan. 30, 2004). "The structural basis for autoinhibition of FLT3 by the juxtamembrane domain," *Mol Cell* 13(2):169-178.

International Search Report dated Aug. 26, 2014 for PCT Application No. PCT/US2014/028730, filed Mar. 14, 2014, 4 pages.

Kurzrock, R. et al. (May 20, 2003). "Philadelphia chromosome-positive leukemias: from basic mechanisms to molecular therapeutics," *Ann Intern Med* 138(10):819-830.

Liu, L. et al. (Nov. 2012, e-published Aug. 16, 2012). "A novel 7-bromoindirubin with potent anticancer activity suppresses survival of human melanoma cells associated with inhibition of STAT3 and Akt signaling," *Cancer Biol Ther* 13(13):1255-1261.

Liu, L. et al. (Feb. 2014, e-published Nov. 1, 2013). "MLS-2384, a new 6-bromoindirubin derivative with dual JAK/Src kinase inhibitory activity, suppresses growth of diverse cancer cells," *Cancer Biol Ther* 15(2):178-184.

Olivier, D. et al. (Mar. 2008, e-published Jan. 22, 2008). "Photoreactivity of indirubin derivatives," *Photochem Photobiol Sci* 7(3):328-326.

Ostro, M.J. et al. (Aug. 1989). "Use of liposomes as injectable-drug delivery systems," *Am J Hosp Pharm* 46(8):1576-1587.

Rao, K.P. (1995). "Recent developments of collagen-based materials for medical applications and drug delivery systems," *J Biomater Sci Polym Ed* 7(7):623-645.

Smith, C.C. et al. (Apr. 18, 2013, e-published Feb. 21, 2013). "Activity of ponatinib against clinically-relevant AC220-resistant kinase domain mutants of FLT3-ITD," *Blood* 121(16):3165-3171.

Vougogiannopoulou, K. et al. (Oct. 23, 2008, e-published Sep. 25, 2008). "Soluble 3',6-substituted indirubins with enhanced selectivity toward glycogen synthase kinase-3 alter circadian period," *J Med Chem* 51(20):6421-6431.

Written Opinion dated Aug. 26, 2014 for PCT Application No. PCT/US2014/028730, filed Mar. 14, 2014, 11 pages.

U.S. Appl. No. 14/659,286 Office Action dated Jan. 13, 2017.

U.S. Appl. No. 14/659,286 Office Action dated Jul. 7, 2016.

U.S. Appl. No. 14/659,286 Restriction Requirement dated Apr. 20, 2016.

Xingi, E. et al. (Oct. 2009, e-published May 13, 2009). "6-Br-5methylindirubin-3'oxime (5-Me-6-BIO) targeting the leishmanial glycogen synthase kinase-3 (GSK-3) short form affects cell-cycle progression and induces apoptosis-like death: exploitation of GSK-3 for treating leishmaniasis," *International Journal for Parasitology* 39(12):1289-1303.

\* cited by examiner

FIG. 4A
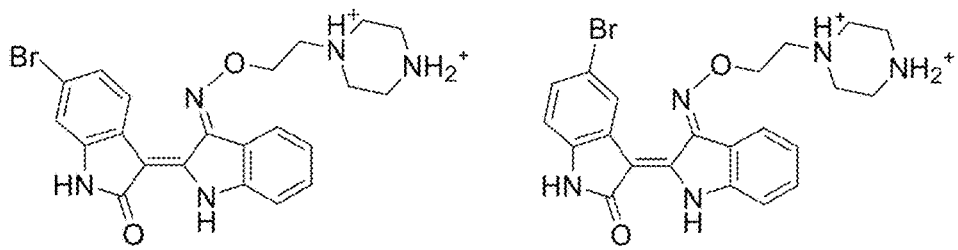
FIG. 4B
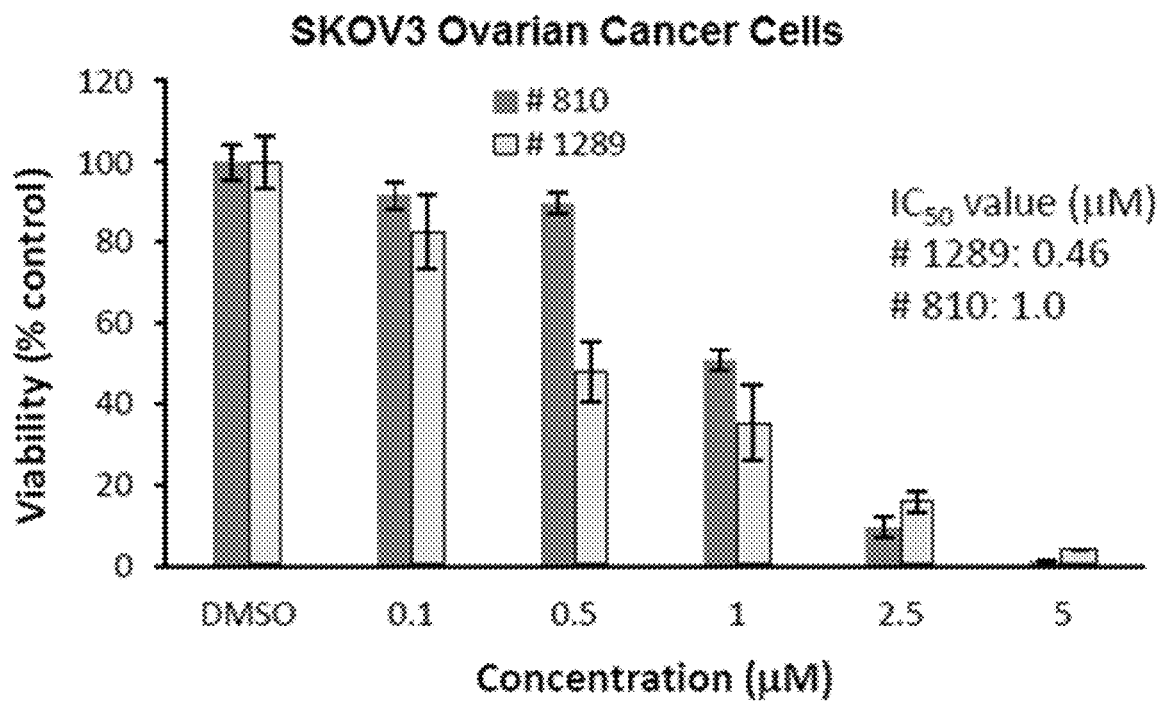
FIG. 4C
IC$_{50}$ Value for
MIA-PaCa Pancreatic
cancer cells
IC$_{50}$ value (µM)
1289: 0.46
810: 0.80

Kinase profiling *in vitro* for # 1276 and # 1289

|  | Compound IC$_{50}$ (nM) | |
|---|---|---|
| Kinase | 1276 | 1289 |
| AKT1 | 3430.00 | 204 |
| BRAF | > 10000 | > 10000 |
| c-Kit | 91.60 | 47.70 |
| c-MET | > 10000 | 8960.00 |
| CDK2/cyclin A | 0.50 | 0.59 |
| EGFR | > 10000 | 348.00 |
| GSK3b | 3.79 | 3.01 |
| IGF1R | 163 | 12.4 |
| KDR/VEGFR2 | 1530 | 17.30 |
| mTOR/FRAP1 | > 10000 | > 10000 |
| ABL1 | 1020 | 71.4 |
| ABL1 (T315I) | 6580 | 214 |
| Aurora A | 954 | 143 |
| c-Src | 34.3 | 3.7 |
| HCK | 304 | 3.36 |
| LYN | 7.95 | 0.83 |
| JAK1 | 56.5 | 33.9 |
| JAK2 | 526 | 47.6 |
| TYK2 | 31.6 | 20.1 |

5-BROMO-INDIRUBINS

CROSS-REFERENCES TO RELATED APPLICATIONS

This application is a continuation of U.S. application Ser. No. 15/898,151, filed Feb. 15, 2018, now abandoned, which is a continuation of U.S. application Ser. No. 14/850,579, filed Sep. 10, 2015, now abandoned, which is a continuation of International Appl. No. PCT/US2014/028730, filed Mar. 14, 2014, which claims the benefit of U.S. Provisional Application No. 61/783,290, filed Mar. 14, 2013, the content of each of which is incorporated by reference herein in its entirety and for all purposes.

BACKGROUND OF THE INVENTION

Cancer is a significant cause of death worldwide. In 2008, cancer accounted for an estimated 13% of worldwide deaths. Lung, prostate, and colorectal cancer are the most common forms of cancer in men and accounted for 40% of all cancers in men in 2008. Breast, colorectal, and cervical cancers made up more than 40% of all cancers in women in the same year. Overall, lung cancer is the most common cancer. Protein kinases are involved in many signal transduction and other cellular processes. Disregulation of kinase activity has been found to be associated with many forms of cancer. Disclosed herein are, inter alia, indirubin derivatives capable of modulating different kinases or single kinases that provide solutions to these and other problems in the art.

BRIEF SUMMARY OF THE INVENTION

Provided herein, inter alia, are compounds, or pharmaceutically acceptable salt thereof, having the formula:

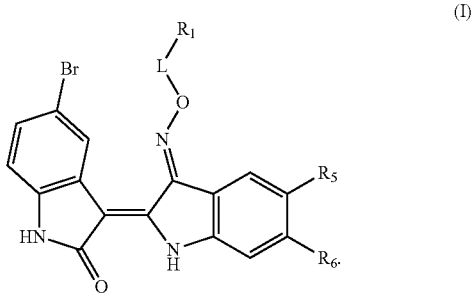

(I)

In the compound of formula (I), L is a bond or substituted or unsubstituted alkylene. $R^1$ is hydrogen, halogen, $-CX^1{}_3$, $-CX^1{}_3$, $-CN$, $-OH$, $-NH_2$, $-COOH$, $-C(O)OR^4$, $-CONH_2$, $-NO_2$, $-SH$, $-NHNH_2$, $-R^2R^3$, $-OR^4$, $-SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^1$ is independently a halogen. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^2$ and $R^3$ are optionally joined together to form a substituted or unsubstituted heterocycloalkyl or substituted or unsubstituted heteroaryl. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ and $R^6$ are independently hydrogen, halogen, $-CX^2{}_3$, $-OCX^2{}_3$, $-CN$, $-OH$, $-NH_2$, $-COOH$, $-C(O)OR^9$, $-CONH_2$, $-NO_2$, $-SH$, $-NHNH_2$, $-NR^7R^8$, $-OR^9$, $-SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^2$ is independently a halogen. $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^7$ and $R^8$ are optionally joined together to form a substituted or unsubstituted heterocycloalkyl or substituted or unsubstituted heteroaryl. $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Also provided herein are pharmaceutical compositions including a pharmaceutically acceptable excipient and a compound, or pharmaceutically acceptable salt thereof, as described herein (e.g. a compound of formula (I) or formula (II), including embodiments thereof).

In another aspect is provided a method of treating cancer by administering an effective amount of a compound, or pharmaceutically acceptable salt thereof, as described herein, including embodiments thereof.

In another aspect is provided a method of modulating the level, activity, or function of a protein associated with a disease. The method includes contacting the protein with an effective amount of a compound, or pharmaceutically acceptable salt thereof, as described herein, including embodiments thereof.

BRIEF DESCRIPTION OF THE DRAWINGS

FIG. 2B depicts MDA-MB-231 (black) and MDA-MB-468 (gray), in order left to right; FIG. 2C: 1 µM (gray); 10 µM (black), in order left to right; FIG. 2D: 1 µM (gray); 10 µM (black), in order left to right;

FIGS. 4A-4C. Effects of compound 1289 and 810 on viabilities of ovarian and pancreatic cancer cells; (FIG. 4A). Structures of compound 1289 (5-bromoindirubin-3'-oxime derivative) and compound 810 (6-bromoindirubin-3'-oxime derivative). As described in FIG. 3, $IC_{50}$ values were determined using MTS assays in SKOV3 ovarian (FIG. 4B) and pancreatic (FIG. 4C) cancer cells; each experiment was performed in quadruplicate. Histogram ordering (left to right): FIG. 4B: #810 (dark gray); #1289 (light gray).

FIG. 7A) effect on A2058 melanoma cells; FIG. 7B) effect on DU145 prostate cancer cells. Histogram ordering (left to right); 0.25 µM, 1 µM, respectively.

FIG. 8A: tumor volume over time in days of treatment; FIG. 8B: histogram of tumor weight for vehicle (left bin) and IRD1281 (right bin)); FIG. 8C: tumor volume over time in days of treatment; FIG. 8D: histogram of tumor weight for vehicle (left bin) and IRD1289 (right bin)) on A549 lung cancer SQ xenografts. Conditions: NSG mice, female; Vehicle group: 10; Treatment group: 10; Oral administration at 25 mg/kg, twice/day. Legend: FIG. 8A: vehicle (diamonds); IRD 1281: squares); FIG. 8C: vehicle (diamonds); IRD 1289 (squares).

DETAILED DESCRIPTION OF THE INVENTION

Figure 1:
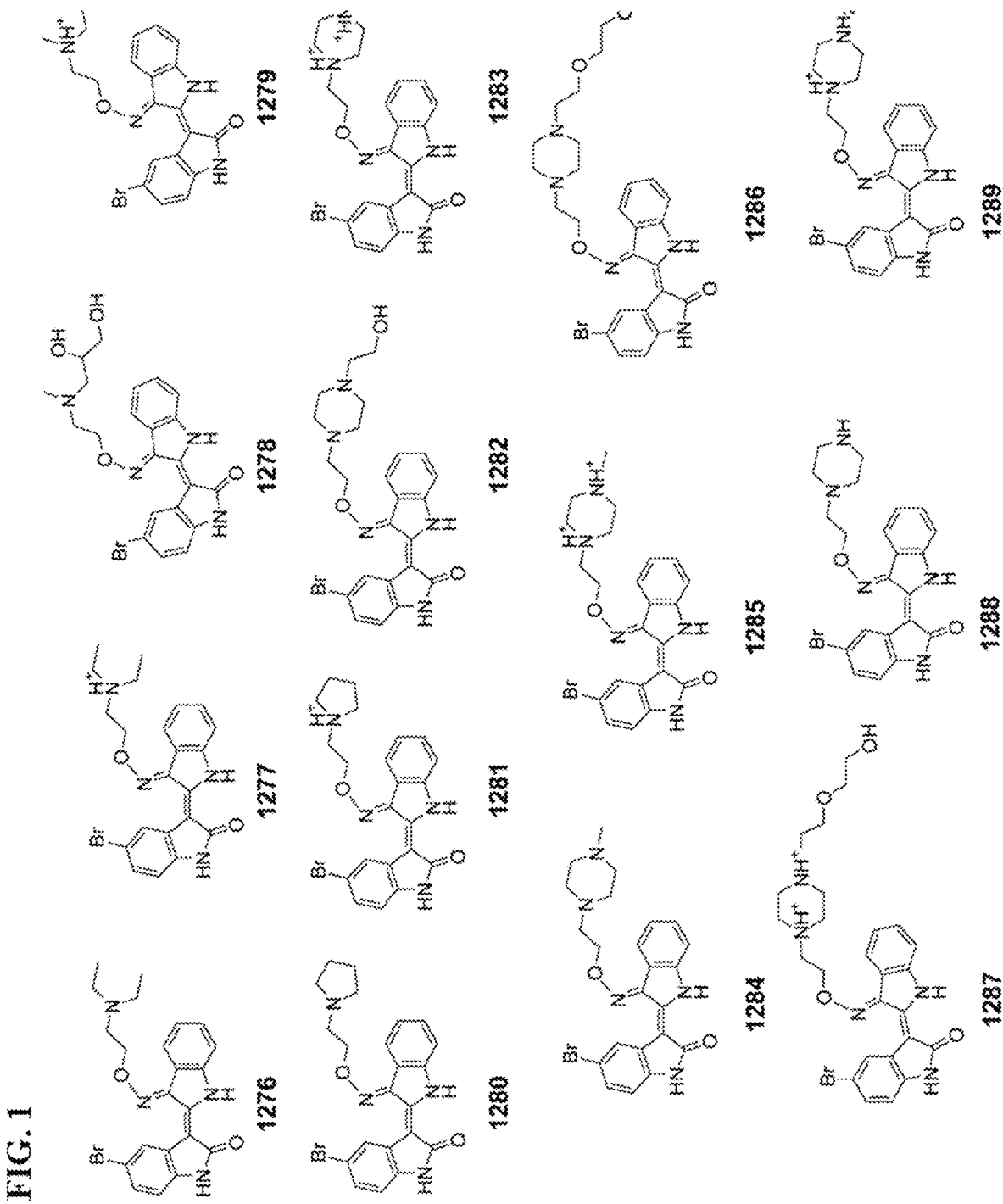
FIG. 1. Structures of 5-bromoindirubin-3'-oxime derivatives (5BIODs).
Figure 2A:
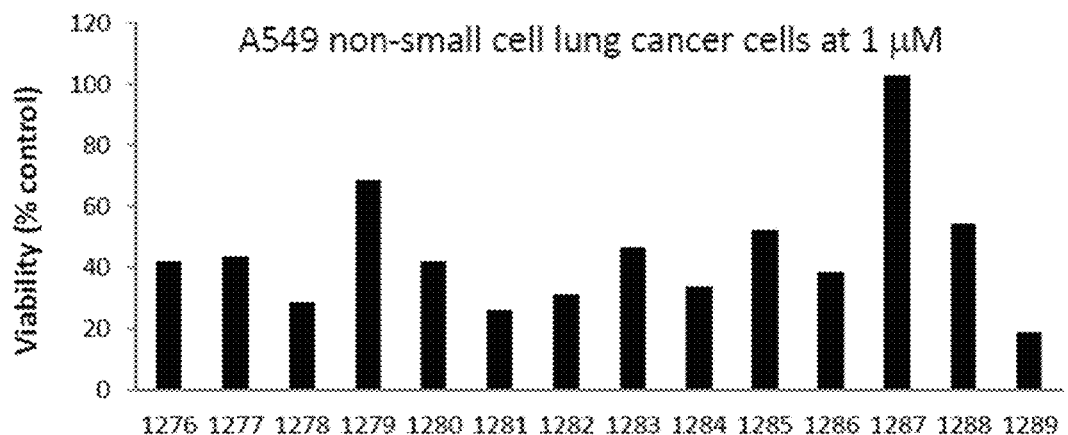
FIGS. 2A-2G. Effects of 5BIODs on viabilities of human cancer cells; MTS assays were performed for cell viability; human A549 non-small cell lung cancer (FIG. 2A), MDA-MB-231 and MDA-MB-468 breast cancer (FIG. 2B), A2058 melanoma (FIG. 2C), DU145 prostate cancer (FIG. 2D), SKOV3 ovarian cancer (FIG. 2E), T315I Abl mutant KCL-22 CML (FIG. 2F) and MIA-PaCa2 pancreatic cancer (FIG. 2G) cells were seeded in 96-well plates (5000/well for solid tumor cell lines and 10000 cells/well for CML cell line), incubated overnight at 37° C. in 5% (v/v) $CO_2$ and exposed to 5BIODs at 1 µM or 10 µM concentration for 48 h; DMSO was used as the vehicle control; cell viability was determined by tetrazolium conversion to its formazan dye and absorbance was measured at 490 nm using an automated ELISA plate reader; each experiment was performed in quadruplicate. Histogram ordering.
Figure 2B:
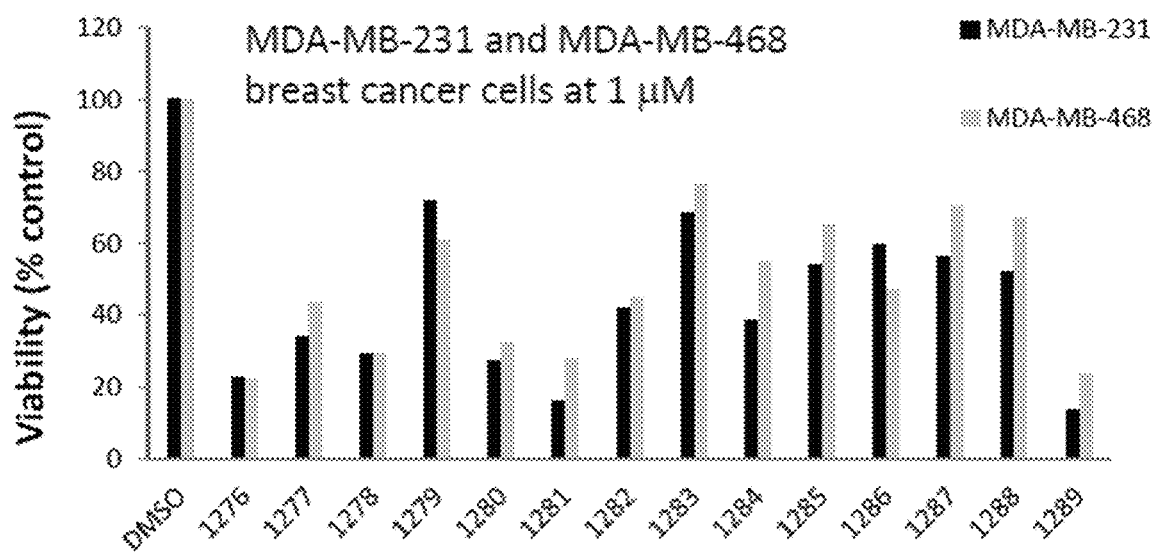
Figure 2C:
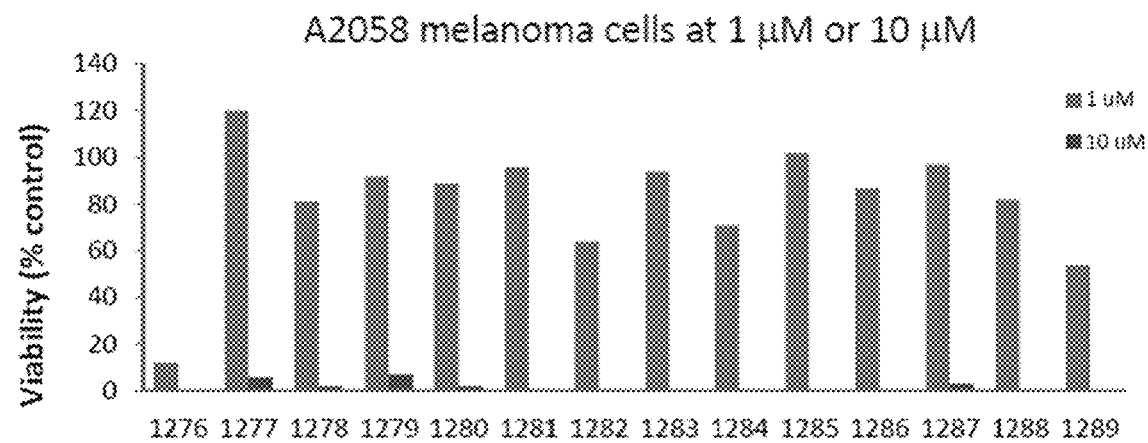
Figure 2D:
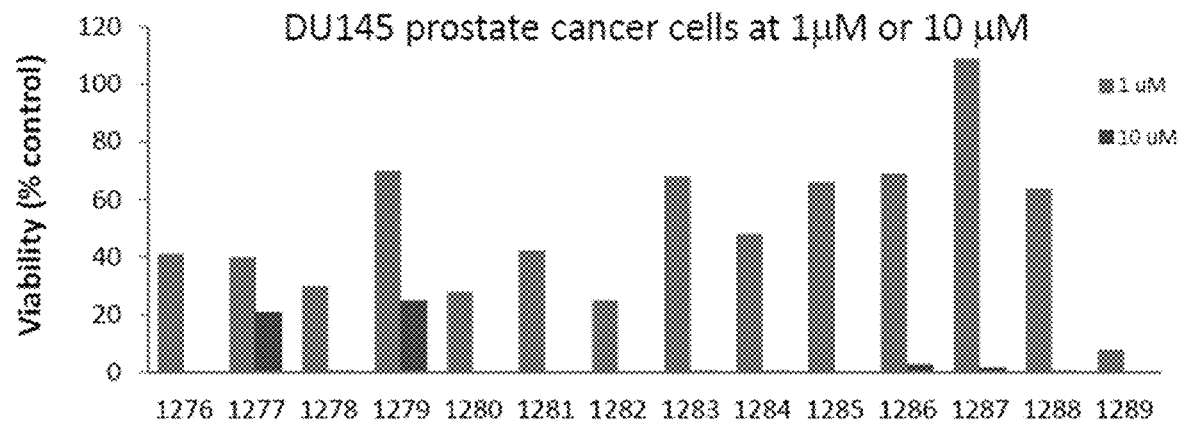
Figure 2E:
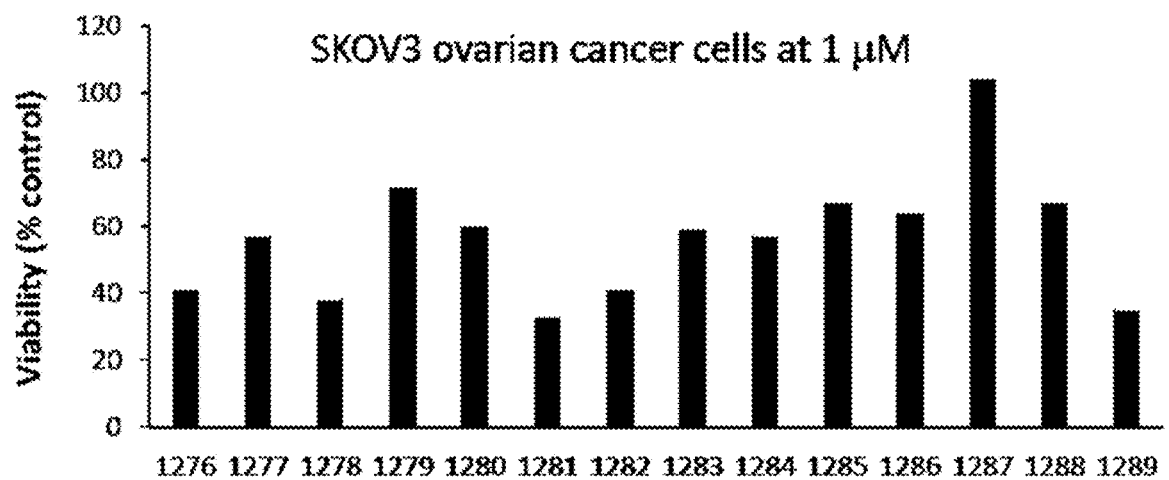
Figure 2F:
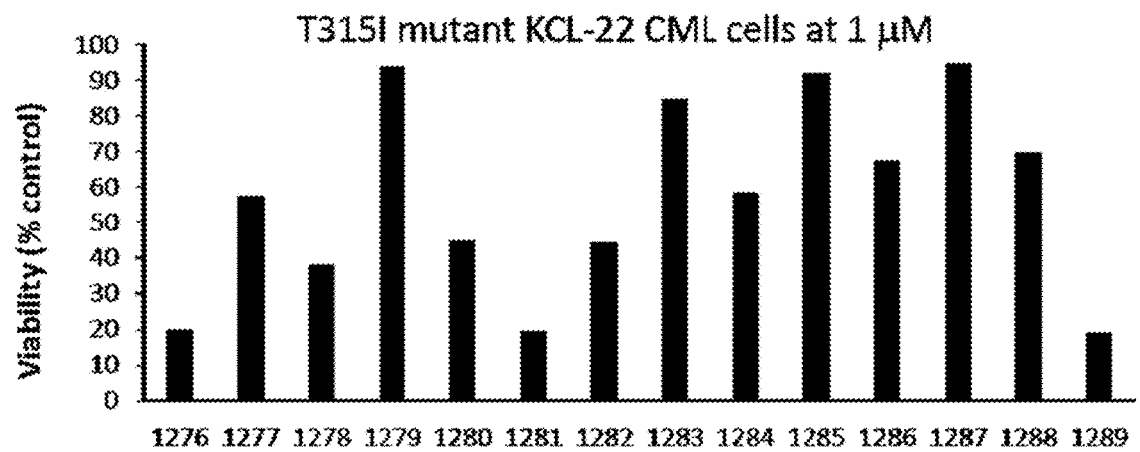
Figure 2G:
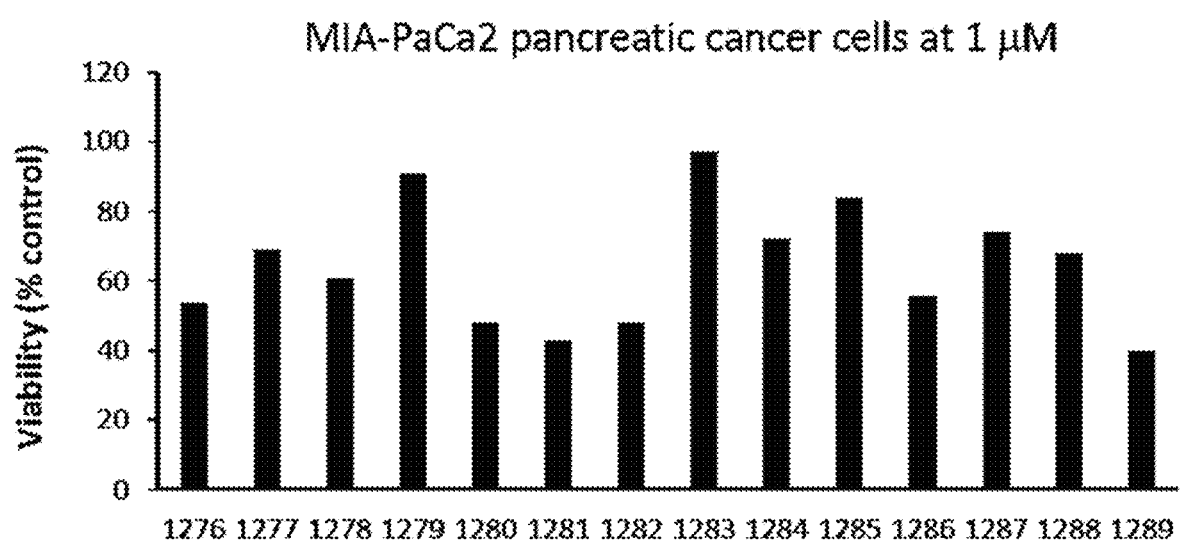
Figure 3:
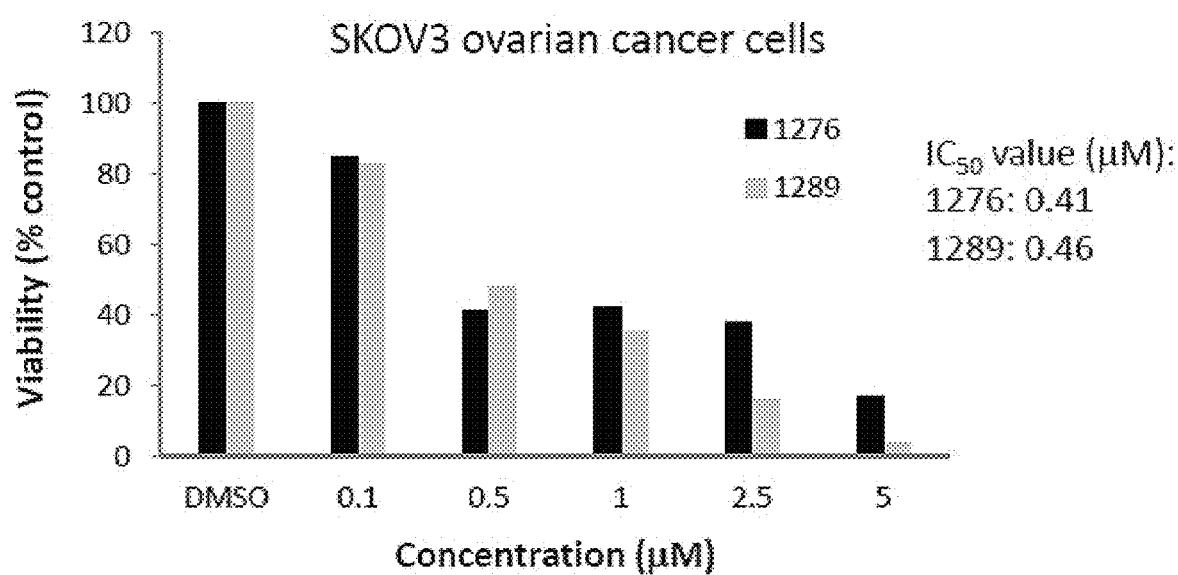
FIG. 3. Compound 1276 and 1289 reduce viabilities of SKOV3 ovarian cancer cells; MTS assays were performed for cell viability as described in FIGS. 2A-2G; $IC_{50}$ values were determined; each experiment was performed in quadruplicate. Histogram ordering (left to right): 1276 (black); 1289 (gray).

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH=CH—O—CH₃, —Si(CH₃)₃, —CH₂—CH=N—OCH₃, —CH=CH—N(CH₃)—CH₃, —O—CH₃, —O—CH₂—CH₃, and —CN. Up to two or three heteroatoms may be consecutive, such as, for example, —CH₂—NH—OCH₃ and —CH₂—O—Si(CH₃)₃.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. A 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and -CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating sub stituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_2$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:
(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or " size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or " lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl.

In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C-$ or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$ or carbon-14 ($^{14}C$). All isotopic variations of the compounds of the present invention, whether radioactive or not, are encompassed within the scope of the present invention.

The symbol "~~~" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of sub stituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters;

including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, reduce one or more symptoms of a disease or condition, reduce the level of a kinase activity in a cell (e.g. JAK2, Src, STAT3, ABL1, T35I mutant ABL1, TYK2, Aurora A, cylin dependent kinase, or GSK-3(3). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. JAK, JAK2, TYK2, c-Src, ABL1, T315I mutant ABL1, Aurora A, GSK-3β, CDK). In embodiments contacting includes allowing a compound described herein to interact with a protein or enzyme that is involved in a signaling pathway (e.g. STAT3 pathway).

As defined herein, the term "inhibition", "inhibit", "inhibiting" and the like in reference to a protein-inhibitor interaction means negatively affecting (e.g. decreasing) the activity or function of the protein (e.g. decreasing the phosphorylation of another protein by a kinase) relative to the activity or function of the protein (e.g. kinase) in the absence of the inhibitor (e.g. kinase inhibitor or kinase inhibitor compound). In embodiments inhibition refers to reduction of a disease or symptoms of disease. In embodiments, inhibition refers to a reduction in the activity of a signal transduction pathway or signaling pathway (e.g. reduction of a pathway involving JAK, JAK2, TYK2, c-Src, ABL1, T315I mutant ABL1, Aurora A, GSK-3β, CDK, STAT, or STAT3). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. JAK, JAK2, TYK2, c-Src, ABL1, T3 151I mutant ABL1, Aurora A, GSK-3β, CDK, STAT, or STAT3). In embodiments, JAK, JAK2, TYK2, c-Src, ABL1, T315I mutant ABL1, Aurora A, GSK-3β, CDK, STAT, or STAT3 is a human protein.

The term "modulator" refers to a composition that increases or decreases the level of a target molecule or the function of a target molecule (e.g. a target may be a kinase (e.g. a JAK, JAK2, TYK2, c-Src, ABL1, T315I mutant ABL1, Aurora A, GSK-3β, CDK) and the function may be to phosphorylate a molecule or the target may be a kinase (e.g. a JAK, JAK2, TYK2, c-Src, ABL1, T315I mutant ABL1, Aurora A, GSK-3β, CDK) and the function may be the function of a downstream signaling pathway including a STAT or STAT3). In embodiments, a kinase modulator is a compound that reduces the activity of a kinase in a cell. A kinase modulator may reduce the activity of one kinase but cause an increase in enzyme activity of another kinase that results in a reduction or increase, respectively, of cell growth and proliferation. In embodiments, a kinase disease modulator is a compound that reduces the severity of one or more symptoms of a disease associated with the kinase (e.g. cancer).

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human.

"Disease" or "condition" refer to a state of being or health status of a patient or subject capable of being treated with a compound, pharmaceutical composition, or method provided herein. In embodiments, the disease is a disease related to (e.g. caused by) an activated or overactive kinase or aberrant kinase activity as described herein. In embodiments, the disease is a disease related to (e.g. characterized by) an inhibited kinase or reduced kinase activity (e.g. cancer with decreased level of a JAK, JAK2, TYK2, c-Src, ABL1, T315I mutant ABL1, Aurora A, GSK-3β, or CDK activity or decreased signal transduction activity in pathways involving a JAK, JAK2, TYK2, c-Src, ABL1, T315I mutant ABL1, Aurora A, GSK-3β, CDK, a STAT, or STAT3). Examples of diseases, disorders, or conditions include, but are not limited to, cancer, lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma. In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma.

As used herein, the term "cancer" refers to all types of cancer, neoplasm or malignant tumors found in mammals, including leukemia, lymphoma, carcinomas and sarcomas.

Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER$^2$ positive, doxorubicin resistant, tamoxifen resistant, ductal carcinoma, lobular carcinoma, primary, metastatic), ovarian cancer, pancreatic cancer, liver cancer (e.g.hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

The term "associated" or "associated with" in the context of a substance or substance activity or function associated with a disease (e.g. a protein associated disease, a cancer associated with aberrant kinase activity) means that the disease (e.g. cancer) is caused by (in whole or in part), or a symptom of the disease is caused by (in whole or inpart) the substance or substance activity or function. For example, a cancer associated with aberrant kinase activity or function may be a cancer that results (entirely or partially) or is otherwise characterized by aberrant kinase activity or function (e.g. enzyme activity, protein-protein interaction, signaling pathway) or a cancer wherein a particular symptom of the disease is caused (entirely or partially) by aberrant kinase activity or function. As used herein, what is described as being associated with a disease, if a causative agent, could be a target for treatment of the disease. For example, a cancer associated with aberrant kinase activity or function or a kinase associated cancer, may be treated with a kinase modulator or kinase inhibitor, in the instance where increased kinase activity or function (e.g. signaling pathway activity) causes the cancer.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a kinase with a compound as described herein may result in a change in one or more protein-protein interactions of the kinase, resulting in changes in cell growth, proliferation, or survival.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal).

Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

The compounds described herein can be used in combination with one another, with other active agents known to be useful in treating a disease associated with cells expressing a particular kinase as described herein, or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another.

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The compositions of the present invention can also be delivered as microspheres for slow release in the body. For example, microspheres can be administered via intradermal injection of drug-containing microspheres, which slowly release subcutaneously (see Rao, *J. Biomater. Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Pharmaceutical compositions provided by the present invention include compositions wherein the active ingredient (e.g. compounds described herein, including embodiments thereof) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule such as a kinase described herein, and/or reducing, eliminating, or slowing the progression of disease symptoms (e.g. cancer growth or metastasis). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. cancer, lung cancer, breast cancer, ovarian cancer, leukemia, melanoma, pancreatic cancer, or prostate cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318026, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142266, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixiimab; decitabine; dehydrodidemnin B; deslorelin; dexamethasone; dexifosfamide; dexrazoxane; dexverapamil; diazi-quone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or r1L.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9265B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700

(Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (-)-Phenylahistin (i.e. NSCL-96F037), D-62638 (Asta Medica), D-62636 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER$^{2,}$ anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE726, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER$^{2,}$ anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, 67Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{126}$Re, $^{211}$At, and $^{212}$Bi, optionally conjugated to antibodies directed against tumor antigens.

I. COMPOSITIONS

Provided herein are compounds, or pharmaceutically acceptable salt thereof, having the formula:

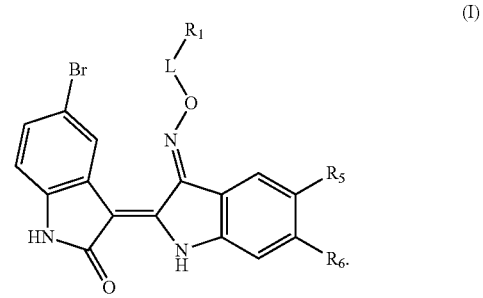

(I)

In the compound of formula (I), L is a bond, substituted or unsubstituted alkylene, or substituted or unsubstituted heteroalkylene. $R^1$ is hydrogen, halogen, —$CX^1_3$, —$OCX^1_3$, —CN, —OH, —$NH_2$, —COOH, —C(O)O$R^4$, —CON$H_2$, —$NO_2$, —SH, —NHN$H_2$, —N$R^2R^3$, —O$R^4$, —S$R^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^1$ is independently a halogen. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^2$ and $R^3$ are optionally joined together to form a substituted or unsubstituted heterocycloalkyl or substituted or unsubstituted heteroaryl. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$R^5$ and $R^6$ are independently hydrogen, halogen, —$CX^2_3$, —$OCX^2_3$, —CN, —OH, —$NH_2$, —COOH, —C(O)$OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^2$ is independently a halogen. $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or $R^7$ and $R^8$ are optionally joined together to form a substituted or unsubstituted heterocycloalkyl or substituted or unsubstituted heteroaryl. $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Provided herein are compounds, or pharmaceutically acceptable salt thereof, having the formula:

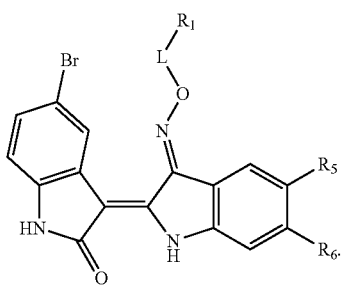

(I)

In the compound of formula (I), L is a bond or substituted or unsubstituted alkylene. $R^1$ is hydrogen, halogen, —$CX^1_3$, —$OCX^1_3$, —CN, —OH, —$NH_2$, —COOH, —C(O)$OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^1$ is independently a halogen. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^2$ and $R^3$ are optionally joined together to form a substituted or unsubstituted heterocycloalkyl or substituted or unsubstituted heteroaryl. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ and $R^6$ are independently hydrogen, halogen, —$CX^2_3$, —$OCX^2_3$, —CN, —OH, —$NH_2$, —COOH, —C(O)$OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^2$ is independently a halogen. $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or $R^7$ and $R^8$ are optionally joined together to form a substituted or unsubstituted heterocycloalkyl or substituted or unsubstituted heteroaryl. $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, L is substituted or unsubstituted alkylene. L may be unsubstituted alkylene. L may be unsubstituted $C_1$-$C_8$ alkylene. L may be unsubstituted $C_1$-$C_4$ alkylene. L may be unsubstituted $C_2$ alkylene. L may be unsubstituted methylene. In embodiments, L is a bond. In embodiments, L is independently a bond or $R^{47}$-substituted or unsubstituted alkylene.

$R^{47}$ is independently oxo, halogen, —$CF_3$, —CN, —OH, —$NH_2$, —COOH, —$CONH_2$, —$NO_2$, —SH, —$SO_2Cl$, —$SO_3H$, —$O_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl.

$R^{48}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —NH $SO_2H$, —NHC(O)H, —NHC(O)OH, —NHOH, —$OCF_3$, —$OCHF_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In embodiments, $R^1$ is halogen, —$CX^1_3$, —$OCX^1_3$, —CN, —OH, —$NH_2$, —COOH, —C(O)$OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $X^1$ is independently —F. In embodiments, $X^1$ is independently —Cl. In embodiments, $X^1$ is independently —I. In embodiments, $X^1$ is independently —Br. In embodiments, $R^1$ is —$NR^2R^3$. In embodiments, $R^1$ is substituted alkyl. $R^1$ may be substituted $C_1$-$C_8$ alkyl. In embodiments, $R^1$ is substituted $C_1$-$C_4$ alkyl. $R^1$ may be substituted ethyl. In embodiments, $R^1$ is a substituted methyl. In embodiments, $R^1$ is not hydrogen.

In embodiments, $R^1$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^1$ is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

$R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{21}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In embodiments, $R^2$ is independently substituted or unsubstituted alkyl. $R^2$ may independently be substituted or unsubstituted $C_1$-$C_8$ alkyl. $R^2$ may independently be substituted $C_1$-$C_8$ alkyl. $R^2$ may independently be unsubstituted $C_1$-$C_8$ alkyl. $R^2$ may independently be substituted or unsubstituted $C_1$-$C_4$ alkyl. $R^2$ may independently be substituted $C_1$-$C_4$ alkyl. $R^2$ may independently be unsubstituted $C_1$-$C_4$ alkyl. $R^2$ may independently be —OH substituted or unsubstituted $C_1$-$C_4$ alkyl. $R^2$ may independently be substituted or unsubstituted methyl. $R^2$ may independently be substituted or unsubstituted ethyl. $R^2$ may independently be substituted or unsubstituted propyl. In embodiments, $R^2$ is independently $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

In embodiments, $R^2$ is substituted or unsubstituted $C_1$-$C_{20}$ alkyl. $R^2$ may be $R^{23}$-substituted or unsubstituted $C_1$-$C_{20}$ alkyl. $R^2$ may be substituted or unsubstituted $C_1$-$C_{10}$ alkyl. $R^2$ may be $R^{23}$-substituted or unsubstituted $C_1$-$C_{10}$ alkyl. $R^2$ may be substituted or unsubstituted $C_1$-$C_8$ alkyl. $R^2$ may be $R^{23}$-substituted or unsubstituted $C_1$-$C_8$ alkyl. $R^2$ may be substituted or unsubstituted $C_1$-$C_5$ alkyl. $R^2$ may be $R^{23}$-substituted or unsubstituted $C_1$-$C_5$ alkyl.

In embodiments, $R^2$ is substituted or unsubstituted 2 to 20 membered heteroalkyl. $R^2$ may be $R^{23}$-substituted or unsubstituted 2 to 20 membered heteroalkyl. $R^2$ may be substituted or unsubstituted 2 to 10 membered heteroalkyl. $R^2$ may be $R^{23}$-substituted or unsubstituted 2 to 10 membered heteroalkyl. $R^2$ may be substituted or unsubstituted 2 to 8 membered heteroalkyl. $R^2$ may be $R^{23}$-substituted or unsubstituted 2 to 8 membered heteroalkyl. $R^2$ may be substituted or unsubstituted 2 to 6 membered heteroalkyl. $R^2$ may be $R^{23}$-substituted or unsubstituted 2 to 6 membered heteroalkyl.

In embodiments, $R^2$ is substituted or unsubstituted 3 to 20 membered cycloalkyl. $R^2$ may be $R^{23}$-substituted or unsubstituted 3 to 20 membered cycloalkyl. $R^2$ may be substituted or unsubstituted 3 to 10 membered cycloalkyl. $R^2$ may be $R^{23}$-substituted or unsubstituted 3 to 10 membered cycloalkyl. $R^2$ may be substituted or unsubstituted 3 to 8 membered cycloalkyl. $R^2$ may be $R^{23}$-substituted or unsubstituted 3 to 8 membered cycloalkyl. $R^2$ may be substituted or unsubstituted 3 to 6 membered cycloalkyl. $R^2$ may be $R^{23}$-substituted or unsubstituted 3 to 6 membered cycloalkyl. $R^2$ may be substituted or unsubstituted 5 membered cycloalkyl. $R^2$ may be $R^{23}$-substituted or unsubstituted 5 membered cycloalkyl. $R^2$ may be substituted or unsubstituted 6 membered cycloalkyl. $R^2$ may be $R^{23}$-substituted or unsubstituted 6 membered cycloalkyl.

In embodiments, $R^2$ is substituted or unsubstituted 3 to 20 membered heterocycloalkyl. $R^2$ may be $R^{23}$-substituted or unsubstituted 3 to 20 membered heterocycloalkyl. $R^2$ may be substituted or unsubstituted 3 to 10 membered heterocycloalkyl. $R^2$ may be $R^{23}$-substituted or unsubstituted 3 to 10 membered heterocycloalkyl. $R^2$ may be substituted or unsubstituted 3 to 8 membered heterocycloalkyl. $R^2$ may be $R^{23}$-substituted or unsubstituted 3 to 8 membered heterocycloalkyl. $R^2$ may be substituted or unsubstituted 3 to 6 membered heterocycloalkyl. $R^2$ may be $R^{23}$-substituted or unsubstituted 3 to 6 membered heterocycloalkyl. $R^2$ may be substituted or unsubstituted 5 membered heterocycloalkyl. $R^2$ may be $R^{23}$-substituted or unsubstituted 5 membered heterocycloalkyl. $R^2$ may be substituted or unsubstituted 6 membered heterocycloalkyl. $R^2$ may be $R^{23}$-substituted or unsubstituted 6 membered heterocycloalkyl.

In embodiments, $R^2$ is substituted or unsubstituted 5 to 10 membered aryl. $R^2$ may be $R^{23}$-substituted or unsubstituted 5 to 10 membered aryl. $R^2$ may be substituted or unsubstituted 5 to 8 membered aryl. $R^2$ may be $R^{23}$-substituted or unsubstituted 5 to 8 membered aryl. $R^2$ may be substituted or unsubstituted 6 membered aryl. $R^2$ may be $R^{23}$-substituted or unsubstituted 6 membered aryl.

In embodiments, $R^2$ is substituted or unsubstituted 5 to 10 membered heteroaryl. $R^2$ may be $R^{23}$-substituted or unsubstituted 5 to 10 membered heteroaryl. $R^2$ may be substituted or unsubstituted 5 to 8 membered heteroaryl. $R^2$ may be $R^{23}$-substituted or unsubstituted 5 to 8 membered heteroaryl. $R^2$ may be substituted or unsubstituted 6 membered heteroaryl. $R^2$ may be $R^{23}$-substituted or unsubstituted 6 membered heteroaryl.

$R^{23}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. $R^{23}$ may independently be —OH. $R^{23}$ may independently be unsubstituted methyl. $R^{23}$ may independently be $R^{24}$-substituted or unsubstituted heteroalkyl. $R^{23}$ may independently be $R^{24}$-substituted or unsubstituted alkyl. $R^{23}$ may independently be $R^{24}$-substituted or unsubstituted $C_1$-$C_4$ alkyl.

$R^{24}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. $R^{24}$ may independently be —OH.

In embodiments, $R^3$ is independently substituted or unsubstituted alkyl. $R^3$ may independently be substituted or unsubstituted $C_1$-$C_8$ alkyl. $R^3$ may independently be substituted $C_1$-$C_8$ alkyl. $R^3$ may independently be unsubstituted $C_1$-$C_8$ alkyl. $R^3$ may independently be substituted or unsubstituted $C_1$-$C_4$ alkyl. $R^3$ may independently be substituted $C_1$-$C_4$ alkyl. $R^3$ may independently be unsubstituted $C_1$-$C_4$ alkyl. $R^3$ may independently be —OH substituted or unsubstituted $C_1$-$C_4$ alkyl. $R^3$ may independently be substituted or unsubstituted methyl. $R^3$ may independently be substituted or unsubstituted ethyl. $R^3$ may independently be substituted or unsubstituted propyl. In embodiments, $R^3$ is independently $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In embodiments, $R^3$ is substituted or unsubstituted $C_1$-$C_{20}$ alkyl. $R^3$ may be $R^{26}$-substituted or unsubstituted $C_1$-$C_{20}$ alkyl. $R^3$ may be substituted or unsubstituted $C_1$-$C_{10}$ alkyl. $R^3$ may be $R^{26}$-substituted or unsubstituted $C_1$-$C_{10}$ alkyl. $R^3$ may be substituted or unsubstituted $C_1$-$C_8$ alkyl. $R^3$ may be $R^{26}$-substituted or unsubstituted $C_1$-$C_8$ alkyl. $R^3$ may be substituted or unsubstituted $C_1$-$C_5$ alkyl. $R^3$ may be $R^{26}$-substituted or unsubstituted $C_1$-$C_5$ alkyl.

In embodiments, $R^3$ is substituted or unsubstituted 2 to 20 membered heteroalkyl. $R^3$ may be $R^{26}$-substituted or unsubstituted 2 to 20 membered heteroalkyl. $R^3$ may be substituted or unsubstituted 2 to 10 membered heteroalkyl. $R^3$ may be $R^{26}$-substituted or unsubstituted 2 to 10 membered heteroalkyl. $R^3$ may be substituted or unsubstituted 2 to 8 membered heteroalkyl. $R^3$ may be $R^{26}$-substituted or unsubstituted 2 to 8 membered heteroalkyl. $R^3$ may be substituted or unsubstituted 2 to 6 membered heteroalkyl. $R^3$ may be $R^{26}$-substituted or unsubstituted 2 to 6 membered heteroalkyl.

In embodiments, $R^3$ is substituted or unsubstituted 3 to 20 membered cycloalkyl. $R^3$ may be $R^{26}$-substituted or unsubstituted 3 to 20 membered cycloalkyl. $R^3$ may be substituted or unsubstituted 3 to 10 membered cycloalkyl. $R^3$ may be $R^{26}$-substituted or unsubstituted 3 to 10 membered cycloalkyl. $R^3$ may be substituted or unsubstituted 3 to 8 membered cycloalkyl. $R^3$ may be $R^{26}$-substituted or unsubstituted 3 to 8 membered cycloalkyl. $R^3$ may be substituted or unsubstituted 3 to 6 membered cycloalkyl. $R^3$ may be $R^{26}$-substituted or unsubstituted 3 to 6 membered cycloalkyl. $R^3$ may be substituted or unsubstituted 5 membered cycloalkyl. $R^3$ may be $R^{26}$-substituted or unsubstituted 5 membered cycloalkyl. $R^3$ may be substituted or unsubstituted 6 membered cycloalkyl. $R^3$ may be $R^{26}$-substituted or unsubstituted 6 membered cycloalkyl.

In embodiments, $R^3$ is substituted or unsubstituted 3 to 20 membered heterocycloalkyl. $R^3$ may be $R^{26}$-substituted or unsubstituted 3 to 20 membered heterocycloalkyl. $R^3$ may be substituted or unsubstituted 3 to 10 membered heterocycloalkyl. $R^3$ may be $R^{26}$-substituted or unsubstituted 3 to 10 membered heterocycloalkyl. $R^3$ may be substituted or unsubstituted 3 to 8 membered heterocycloalkyl. $R^3$ may be $R^{26}$-substituted or unsubstituted 3 to 8 membered heterocycloalkyl. $R^3$ may be substituted or unsubstituted 3 to 6 membered heterocycloalkyl. $R^3$ may be $R^{26}$-substituted or unsubstituted 3 to 6 membered heterocycloalkyl. $R^3$ may be substituted or unsubstituted 5 membered heterocycloalkyl. $R^3$ may be $R^{26}$-substituted or unsubstituted 5 membered heterocycloalkyl. $R^3$ may be substituted or unsubstituted 6 membered heterocycloalkyl. $R^3$ may be $R^{26}$-substituted or unsubstituted 6 membered heterocycloalkyl.

In embodiments, $R^3$ is substituted or unsubstituted 5 to 10 membered aryl. $R^3$ may be $R^{26}$-substituted or unsubstituted 5 to 10 membered aryl. $R^3$ may be substituted or unsubstituted 5 to 8 membered aryl. $R^3$ may be $R^{26}$-substituted or unsubstituted 5 to 8 membered aryl. $R^3$ may be substituted or unsubstituted 6 membered aryl. $R^3$ may be $R^{26}$-substituted or unsubstituted 6 membered aryl.

In embodiments, $R^3$ is substituted or unsubstituted 5 to 10 membered heteroaryl. $R^3$ may be $R^{26}$-substituted or unsubstituted 5 to 10 membered heteroaryl. $R^3$ may be substituted or unsubstituted 5 to 8 membered heteroaryl. $R^3$ may be $R^{26}$-substituted or unsubstituted 5 to 8 membered heteroaryl. $R^3$ may be substituted or unsubstituted 6 membered heteroaryl. $R^3$ may be $R^{26}$-substituted or unsubstituted 6 membered heteroaryl.

$R^{26}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. $R^{26}$ may independently be —OH. $R^{26}$ may independently be unsubstituted methyl. $R^{23}$ may independently be $R^{24}$-substituted or unsubstituted heteroalkyl. $R^{26}$ may independently be $R^{27}$-substituted or unsubstituted alkyl. $R^{26}$ may independently be $R^{27}$-substituted or unsubstituted $C_1$-$C_4$ alkyl.

$R^{27}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. $R^{27}$ may independently be —OH.

In embodiments, $R^2$ and $R^3$ are joined together to form a substituted or unsubstituted heterocycloalkyl or substituted or unsubstituted heteroaryl. $R^2$ and $R^3$ may be joined together to form a substituted or unsubstituted heterocycloalkyl. $R^2$ and $R^3$ may be joined together to form a substituted or unsubstituted 3 to 8 membered heterocycloalkyl. $R^2$ and $R^3$ may be joined together to form a substituted 3 to 8 membered heterocycloalkyl. $R^2$ and $R^3$ may be joined together to form a substituted or unsubstituted 5 to 7 membered heterocycloalkyl. $R^2$ and $R^3$ may be joined together to form a substituted 5 to 7 membered heterocycloalkyl. $R^2$ and $R^3$ may be joined together to form a substituted or unsubstituted 4 membered heterocycloalkyl. $R^2$ and $R^3$ may be joined together to form a substituted or unsubstituted 5 membered heterocycloalkyl. $R^2$ and $R^3$ may be joined together to form a substituted or unsubstituted 6 membered heterocycloalkyl.

$R^2$ and $R^3$ may be joined together to form a $R^{23}$-substituted or unsubstituted heterocycloalkyl. $R^2$ and $R^3$ may be joined together to form a $R^{23}$-substituted or unsubstituted 5 to 7 membered heterocycloalkyl. $R^2$ and $R^3$ may be joined together to form a $R^{23}$-substituted or unsubstituted 4 membered heterocycloalkyl. $R^2$ and $R^3$ may be joined together to form an $R^{23}$-substituted or unsubstituted 5 to 7 membered heterocycloalkyl, wherein $R^{23}$ is independently a substituted or unsubstituted alkyl or substituted or unsubstituted heteroalkyl. $R^2$ and $R^3$ may be joined together to form an $R^{23}$-substituted 5 to 7 membered heterocycloalkyl, wherein $R^{23}$ is independently a substituted or unsubstituted $C_1$-$C_8$ alkyl or substituted or unsubstituted 2 to 8 membered heteroalkyl.

In embodiments, $R^2$ and $R^3$ are joined together to form a substituted or unsubstituted pyrrolidinyl. In embodiments, $R^2$ and $R^3$ are joined together to form a substituted or unsubstituted piperazinyl. In embodiments, $R^2$ and $R^3$ are joined together to form a $R^{23}$-substituted or unsubstituted pyrrolidinyl. In embodiments, $R^2$ and $R^3$ are joined together to form a $R^{23}$-substituted or unsubstituted piperazinyl. $R^{23}$ is as described herein, including embodiments thereof. In embodiments, $R^2$ and $R^3$ are joined together to form a $R^{24}$-substituted or unsubstituted phthalimidyl.

In embodiments, $R^4$ is independently $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

$R^{29}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NH SO_2H$, —NHC(O)H, —NHC(O)OH, —NHOH, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

$R^{30}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^5$ may independently be halogen, —$CX^2_3$, —$OCX^2_3$, —CN, —OH, —$NH_2$, —COOH, —$C(O)OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^5$ is independently —F. In embodiments, $R^5$ is independently —Cl. In embodiments, $R^5$ is independently —I. In embodiments, $R^5$ is independently —Br. In embodiments, $X^2$ is independently —F. In embodiments, $X^2$ is independently —Cl. In embodiments, $X^2$ is independently —I. In embodiments, $X^2$ is independently —Br. In embodiments, $R^5$ is —$NR^7R^8$.

In embodiments, $R^5$ is —$C(O)OCH_3$. In embodiments, $R^5$ is —$OCH_3$. In embodiments, $R^5$ is —$OCH(CH_3)_2$. In embodiments, $R^5$ is —CN. In embodiments, $R^5$ is —$NO_2$. In embodiments, $R^5$ is —$NH_2$. In embodiments, $R^5$ is halogen. In embodiments, $R^5$ is independently hydrogen. In embodiments, $R^5$ is independently unsubstituted methyl. In embodiments, $R^5$ is independently —$OCF_3$. In embodiments, $R^5$ is independently —NHAc. In embodiments, $R^5$ is independently —OH. In embodiments, $R^5$ is unsubstituted alkyl. $R^5$ may be unsubstituted $C_1$-$C_8$ alkyl. In embodiments, $R^5$ is unsubstituted $C_1$-$C_4$ alkyl. $R^5$ may be unsubstituted ethyl. In embodiments, $R^5$ is an unsubstituted methyl. In embodiments, $R^5$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

In embodiments, $R^5$ is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments $R^5$ is not hydrogen.

Each $R^{32}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

Each $R^{33}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^6$ may independently be halogen, —$CX^2_3$, —$OCX^2_3$, —CN, —OH, —$NH_2$, —COOH, —$C(O)OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^6$ is independently —F. In embodiments, $R^6$ is independently —Cl. In embodiments, $R^6$ is independently —I. In embodiments, $R^6$ is independently —Br. In embodiments, $X^2$ is independently —F. In embodiments, $X^2$ is independently —Cl. In embodiments, $X^2$ is independently —I. In embodiments, $X^2$ is independently —Br. In embodiments, $R^6$ is —$NR^7R^8$.

In embodiments, $R^6$ is —$C(O)OCH_3$. In embodiments, $R^6$ is —$OCH_3$. In embodiments, $R^6$ is —$OCH(CH_3)_2$. In embodiments, $R^6$ is —CN. In embodiments, $R^6$ is —$NO_2$. In embodiments, $R^6$ is —$NH_2$. In embodiments, $R^6$ is halogen. In embodiments, $R^6$ is independently hydrogen. In embodiments, $R^6$ is independently unsubstituted methyl. In embodiments, $R^6$ is independently —$OCF_3$. In embodiments, $R^6$ is independently —NHAc. In embodiments, $R^6$ is independently —OH. In embodiments, $R^6$ is unsubstituted alkyl. $R^6$ may be unsubstituted $C_1$-$C_8$ alkyl. In embodiments, $R^6$ is unsubstituted $C_1$-$C_4$ alkyl. $R^6$ may be unsubstituted ethyl. In embodiments, $R^6$ is an unsubstituted methyl. In embodiments, $R^6$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

In embodiments, $R^6$ is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^5$ and $R^6$ are independently hydrogen. In embodiments, $R^6$ is not hydrogen.

Each $R^{35}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

Each $R^{36}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In embodiments, $R^7$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

$R^{38}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. $R^{38}$ may independently be —OH. $R^{38}$ may independently be unsubstituted methyl. $R^{38}$ may independently be $R^{39}$-substituted or unsubstituted heteroalkyl. $R^{38}$ may independently be $R^{39}$-substituted or unsubstituted alkyl. $R^{38}$ may independently be $R^{39}$-substituted or unsubstituted $C_1$-$C_4$ alkyl.

$R^{39}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^8$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{41}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

$R^{42}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In embodiments, $R^7$ and $R^8$ are joined together to form a substituted or unsubstituted heterocycloalkyl or substituted or unsubstituted heteroaryl. $R^7$ and $R^8$ may be joined together to form a substituted or unsubstituted heterocycloalkyl. $R^7$ and $R^8$ may be joined together to form a substituted or unsubstituted 3 to 8 membered heterocycloalkyl. $R^7$ and $R^8$ may be joined together to form a substituted 3 to 8 membered heterocycloalkyl. $R^7$ and $R^8$ may be joined together to form a substituted or unsubstituted 5 to 7 membered heterocycloalkyl. $R^7$ and $R^8$ may be joined together to form a substituted 5 to 7 membered heterocycloalkyl. $R^7$ and $R^8$ may be joined together to form an $R^{38}$-substituted 5 to 7 membered heterocycloalkyl, wherein $R^{38}$ is as described herein above. $R^7$ and $R^8$ may be joined together to form an $R^{38}$-substituted 5 to 7 membered heterocycloalkyl, wherein $R^{38}$ is independently a substituted or unsubstituted alkyl or substituted or unsubstituted heteroalkyl. $R^7$ and $R^8$ may be joined together to form an $R^{38}$-substituted 5 to 7 membered heterocycloalkyl, wherein $R^{38}$ is independently a substituted or unsubstituted $C_1$-$C_8$ alkyl or substituted or unsubstituted 2 to 8 membered heteroalkyl. $R^7$ and $R^8$ may be joined together to form a substituted or unsubstituted pyrrolidinyl. $R^7$ and $R^8$ may be joined together to form a substituted or unsubstituted piperazinyl.

In embodiments, $R^9$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

$R^{44}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —NH $SO_2H$, —NHC(O)H, —NHC(O)OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, R⁴⁵-substituted or unsubstituted heterocycloalkyl, R⁴⁵-substituted or unsubstituted aryl, or R⁴⁵-substituted or unsubstituted heteroaryl.

R⁴⁵ is independently oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NH SO₂H, —NHC(O)H, —NHC(O)OH, —NHOH, —OCF₃, —OCHF₂, R⁴⁶-substituted or unsubstituted alkyl, R⁴⁶-substituted or unsubstituted heteroalkyl, R⁴⁶-substituted or unsubstituted cycloalkyl, R⁴⁶-substituted or unsubstituted heterocycloalkyl, R⁴⁶-substituted or unsubstituted aryl, or R⁴⁶-substituted or unsubstituted heteroaryl.

Each R²², R²⁵, R²⁸, R³¹, R³⁴, R³⁷, R⁴⁰, R⁴³, R⁴⁶, and R⁴⁹ is independently hydrogen, oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCHF₂, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound of formula (I) is a compound of formula (II):

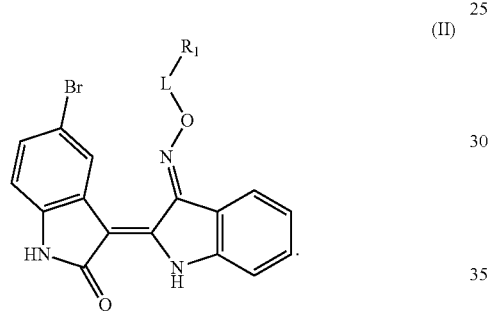
(II)

The compounds, or pharmaceutically acceptable salts thereof, provided herein, may include a protonated nitrogen cation. The compounds, or pharmaceutically acceptable salts thereof, provided herein, may include a plurality of protonated nitrogen cations.

In embodiments, the compound of formula (I) has the formula:

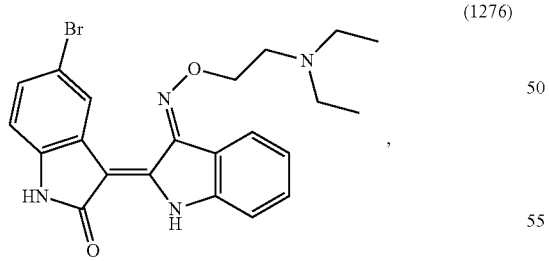
(1276)

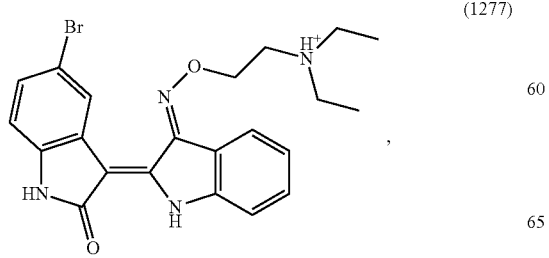
(1277)

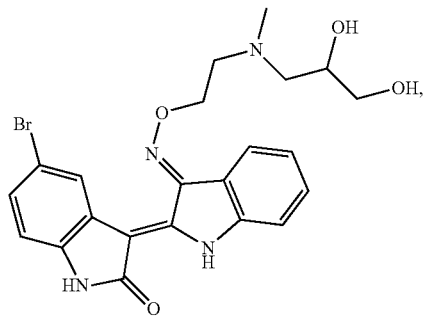
(1278)

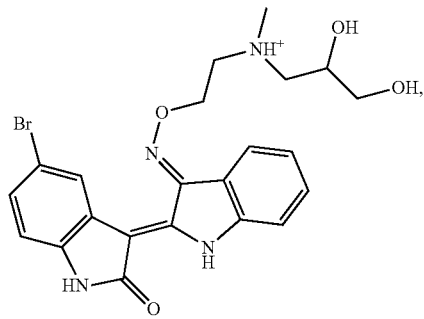
(1279)

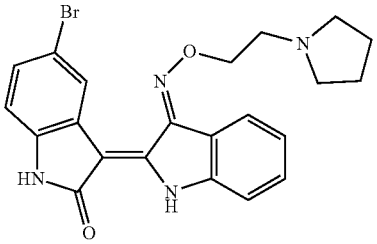
(1280)

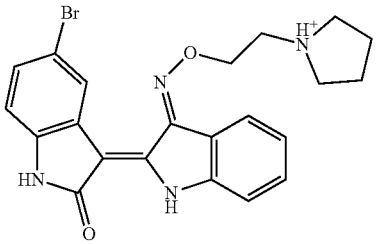
(1281)

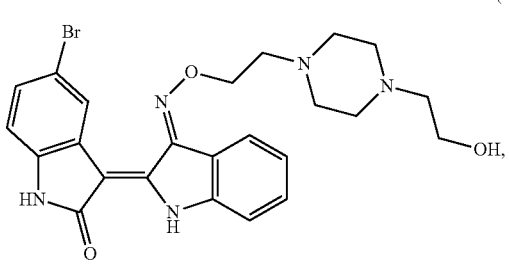
(1282)

(1283)
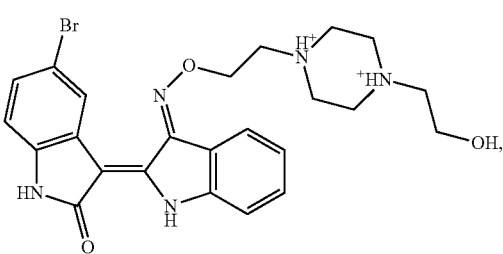
(1284)
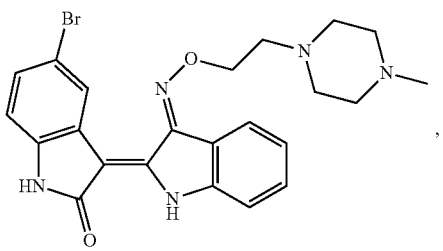
(1285)
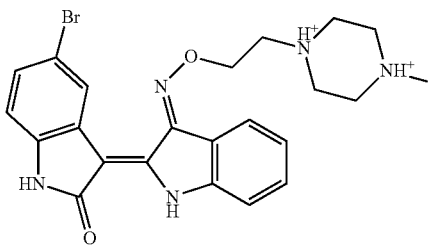
(1286)
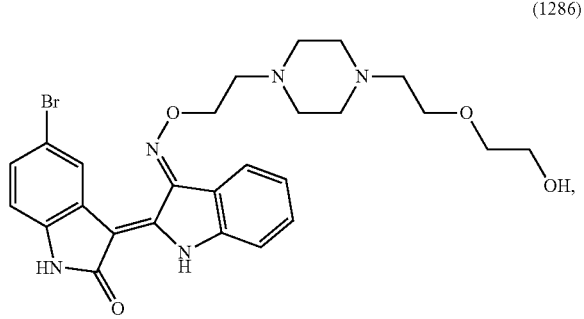
(1287)
(1288)
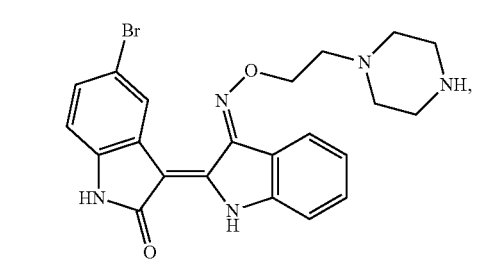
(1289)
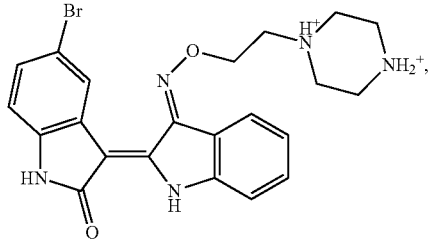
(1501)
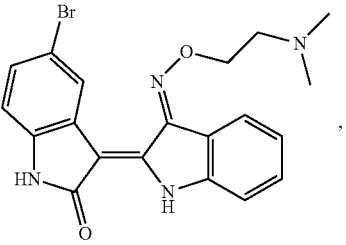
(1501p)
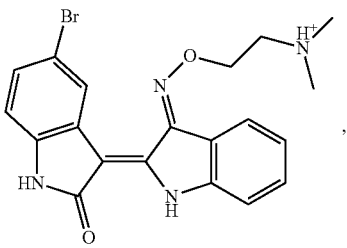
(1502)
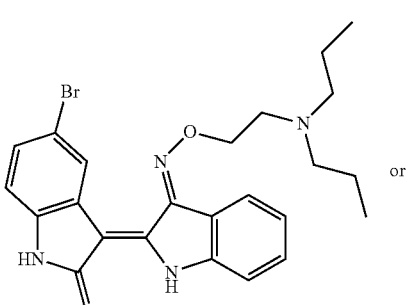
or
(1502p)
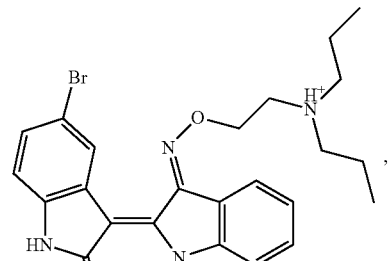
including pharmaceutically acceptable salts thereof.

In embodiments, the compound of formula (I) has the formula:
(XNH5)
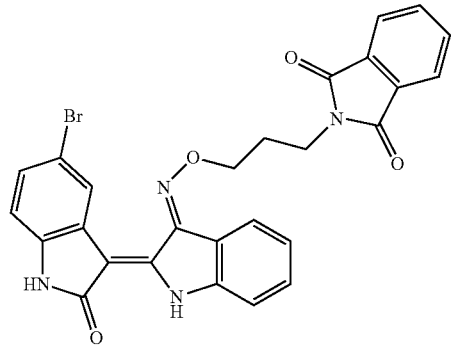
(XNH6)
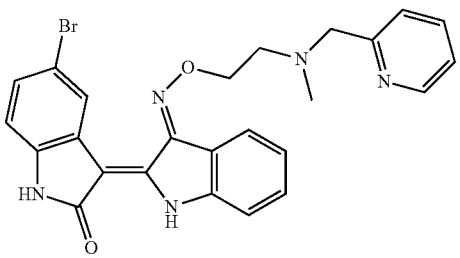
(XNH6p)
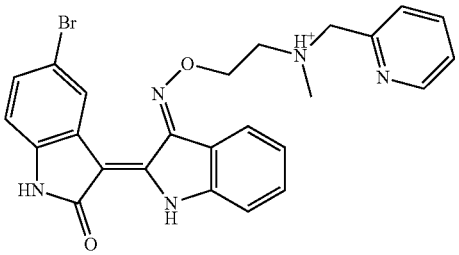
(XNH7)
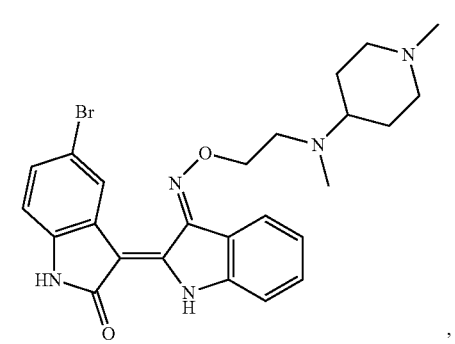
-continued
(XNH7p)
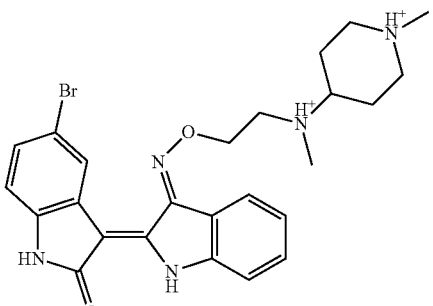
(XNH9)
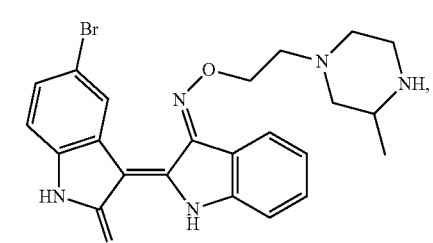
(XNH9p)
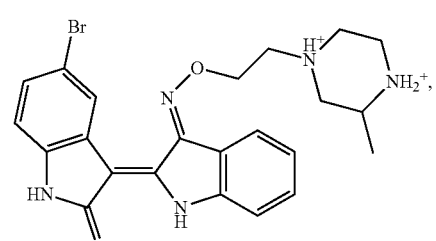
(XNH10)
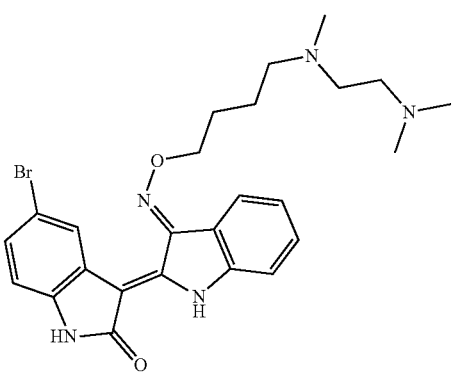
(XNH10p)
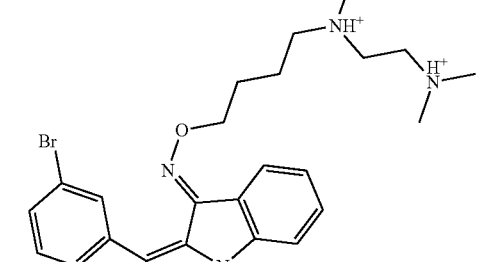

-continued (XNH12)

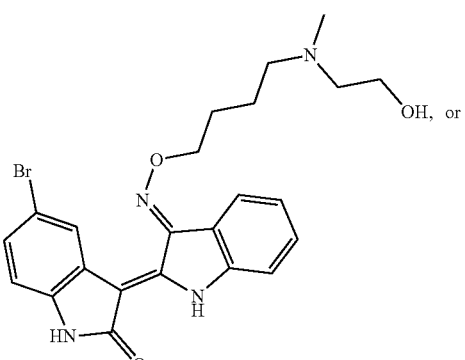

(XNH12p)

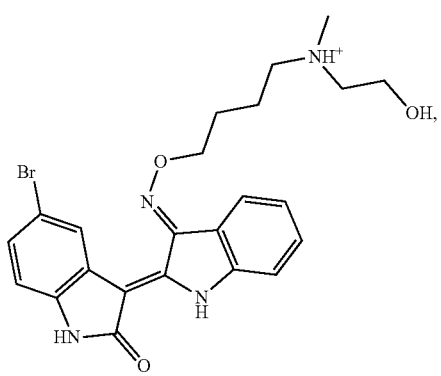

including pharmaceutically acceptable salts thereof.

In embodiments, the compound has the formula 1276, or a pharmaceutically acceptable salt thereof. In embodiments, the compound has the formula 1277, or a pharmaceutically acceptable salt thereof. In embodiments, the compound has the formula 1278, or a pharmaceutically acceptable salt thereof. In embodiments, the compound has the formula 1279, or a pharmaceutically acceptable salt thereof. In embodiments, the compound has the formula 1280, or a pharmaceutically acceptable salt thereof. In embodiments, the compound has the formula 1281, or a pharmaceutically acceptable salt thereof. In embodiments, the compound has the formula 1282, or a pharmaceutically acceptable salt thereof. In embodiments, the compound has the formula 1283, or a pharmaceutically acceptable salt thereof. In embodiments, the compound has the formula 1284, or a pharmaceutically acceptable salt thereof. In embodiments, the compound has the formula 1285, or a pharmaceutically acceptable salt thereof. In embodiments, the compound has the formula 1286, or a pharmaceutically acceptable salt thereof. In embodiments, the compound has the formula 1287, or a pharmaceutically acceptable salt thereof. In embodiments, the compound has the formula 1288, or a pharmaceutically acceptable salt thereof. In embodiments, the compound has the formula 1289. In embodiments, the compound has the formula 1501. In embodiments, the compound has the formula 1501p. In embodiments, the compound has the formula 1502. In embodiments, the compound has the formula 1502p. In embodiments, the compound has the formula XNH5, or a pharmaceutically acceptable salt thereof. In embodiments, the compound has the formula XNH6, or a pharmaceutically acceptable salt thereof. In embodiments, the compound has the formula XNH6p, or a pharmaceutically acceptable salt thereof. In embodiments, the compound has the formula XNH7, or a pharmaceutically acceptable salt thereof. In embodiments, the compound has the formula XNH7p, or a pharmaceutically acceptable salt thereof. In embodiments, the compound has the formula XNH9, or a pharmaceutically acceptable salt thereof. In embodiments, the compound has the formula XNH9p, or a pharmaceutically acceptable salt thereof. In embodiments, the compound has the formula XNH10, or a pharmaceutically acceptable salt thereof. In embodiments, the compound has the formula XNE10p, or a pharmaceutically acceptable salt thereof. In embodiments, the compound has the formula XNH12, or a pharmaceutically acceptable salt thereof. In embodiments, the compound has the formula XNH12p, or a pharmaceutically acceptable salt thereof.

In embodiments, a compound, or pharmaceutically acceptable salts thereof, as described herein may include multiple instances of $R^2$, $R^3$, $R^4$, $R^7$, $R^8$, $R^9$, $R^{20}$ to $R^{49}$, $X^1$, $X^2$, and/or other variables. In such embodiments, each variable may optional be different and be appropriately labeled to distinguish each group for greater clarity. For example, where each $R^2$, $R^3$, $R^4$, $R^7$, $R^8$, $R^9$, $R^{20}$ to $R^{49}$, $X^1$, or $X^2$, is different, they may be referred to, for example, as $R^{2\text{-}1}$, $R^{2.2}$, $R^{2.3}$, $R^{2.4}$, $R^{2.5}$, $R^{2.6}$, $R^{2.7}$, $R^{2.8}$, $R^{2.9}$, $R^{2.10}$, $R^{2.11}$, $R^{2.12}$, $R^{2.13}$, $R^{2.14}$, $R^{2.15}$, $R^{2.16}$, $R^{2.17}$, $R^{2.18}$, $R^{2.19}$, $R^{2.20}$, $R^{2.21}$, $R^{2.22}$, $R^{2.23}$, $R^{2.24}$, $R^{2.25}$, $R^{2.26}$, $R^{2.27}$, $R^{2.28}$, $R^{2.29}$, $R^{2.30}$, $R^{2.31}$, $R^{2.32}$, $R^{2.33}$, $R^{2.34}$, $R^{2.35}$, $R^{2.36}$, $R^{2.37}$, $R^{2.38}$, $R^{2.39}$, $R^{2.40}$, $R^{2.41}$, $R^{2.42}$, $R^{3.1}$, $R^{3.2}$, $R^{3.3}$, $R^{3.4}$, $R^{3.5}$, $R^{3.6}$, $R^{3.7}$, $R^{3.8}$, $R^{3.9}$, $R^{3.10}$, $R^{3.11}$, $R^{3.12}$, $R^{3.13}$, $R^{3.14}$, $R^{3.15}$, $R^{3.16}$, $R^{3.17}$, $R^{3.18}$, $R^{3.19}$, $R^{3.20}$, $R^{3.21}$, $R^{3.22}$, $R^{3.23}$, $R^{3.24}$, $R^{3.25}$, $R^{3.26}$, $R^{3.27}$, $R^{3.28}$, $R^{3.29}$, $R^{3.30}$, $R^{3.31}$, $R^{3.32}$, $R^{3.33}$, $R^{3.34}$, $R^{3.35}$, $R^{3.36}$, $R^{3.37}$, $R^{3.38}$, $R^{3.39}$, $R^{3.40}$, $R^{3.41}$, $R^{3.42}$, $R^{4.1}$, $R^{4.2}$, $R^{4.3}$, $R^{4.4}$, $R^{4.5}$, $R^{4.6}$, $R^{4.7}$, $R^{4.8}$, $R^{4.9}$, $R^{4.10}$, $R^{4.11}$, $R^{4.12}$, $R^{4.13}$, $R^{4.14}$, $R^{4.15}$, $R^{4.16}$, $R^{4.17}$, $R^{4.18}$, $R^{4.19}$, $R^{4.20}$, $R^{4.21}$, $R^{4.22}$, $R^{4.23}$, $R^{4.24}$, $R^{4.25}$, $R^{4.26}$, $R^{4.27}$, $R^{4.28}$, $R^{4.29}$, $R^{4.30}$, $R^{4.31}$, $R^{4.32}$, $R^{4.33}$, $R^{4.34}$, $R^{4.35}$, $R^{4.36}$, $R^{4.37}$, $R^{4.38}$, $R^{4.39}$, $R^{4.40}$, $R^{4.41}$, $R^{4.42}$, $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$ $R^{20.1}$ to $R^{49.1}$ $R^{20.2}$ to $R^{49.2}$ $R^{20.3}$ to $R^{49.3}$ $R^{20.4}$ to $R^{49.4}$ $R^{20.5}$ to $R^{49.5}$ $R^{20.6}$ to $R^{49.6}$ $R^{20.7}$ to $R^{49.7}$, $R^{20.8}$ to $R^{49.8}$, $R^{20.9}$ to $R^{49.9}$, $R^{20.10}$ to $R^{49.10}$, $R^{20.11}$ to $R^{49.11}$, $R^{20.12}$ to $R^{49.12}$, $R^{20.13}$ to $R^{49.13}$, $R^{20.14}$ to $R^{49.14}$, $R^{20.15}$ to $R^{49.15}$, $R^{20.16}$ to $R^{49.16}$, $R^{20.17}$ to $R^{49.17}$, $R^{20.18}$ to $R^{49.18}$, $R^{20.19}$ to $R^{49.19}$, $R^{20.20}$ to $R^{49.20}$, $R^{20.21}$ to $R^{49.21}$ $R^{20.22}$ to $R^{49.22}$ $R^{20.23}$ to $R^{49.23}$ $R^{20.24}$ to $R^{49.24}$ $R^{20.25}$ to $R^{49.25}$ $R^{20.26}$ to $R^{49.26}$ $R^{20.27}$ to $R^{49.27}$, $R^{20.28}$ to $R^{49.28}$, $R^{20.29}$ to $R^{49.29}$, $R^{20.30}$ to $R^{49.30}$, $R^{20.31}$ to $R^{49.31}$, $R^{20.32}$ to $R^{49.32}$, $R^{20.33}$ to $R^{49.33}$, $R^{20.34}$ to $R^{49.34}$ $R^{20.35}$ to $R^{49.35}$ $R^{20.36}$ to $R^{49.36}$ $R^{20.37}$ to $R^{49.37}$ $R^{20.38}$ to $R^{49.38}$ $R^{20.39}$ to $R^{49.39}$ $R^{20.40}$ to $R^{49.40}$, $R^{20.41}$ to $R^{49.41}$, $R^{20.42}$ to $R^{49.42}$, $X^{1.1}$, $X^{1.2}$, $X^{1.3}$, $X^{1.4}$, $X^{1.5}$, $X^{1.6}$, $X^{1.7}$, $X^{1.8}$, $X^{1.9}$, $X^{1.10}$, $X^{1.11}$, $X^{1.12}$, $X^{1.13}$, $X^{1.14}$, $X^{1.15}$, $X^{1.16}$, $X^{1.17}$, $X^{1.18}$, $X^{1.19}$, $X^{1.20}$, $X^{1.21}$, $X^{1.22}$, $X^{1.23}$, $X^{1.24}$, $X^{1.25}$, $X^{1.26}$, $X^{1.27}$, $X^{1.28}$, $X^{1.29}$, $X^{1.30}$, $X^{1.31}$, $X^{1.32}$, $X^{1.33}$, $X^{1.34}$, $X^{1.35}$, $X^{1.36}$, $X^{1.37}$, $X^{1.38}$, $X^{1.39}$, $X^{1.40}$, $X^{1.41}$, $X^{1.42}$, $X^{2.1}$, $X^{2.2}$, $X^{2.3}$, $X^{2.4}$, $X^{2.5}$, $X^{2.6}$, $X^{2.7}$, $X^{2.8}$, $X^{2.9}$, $X^{2.10}$, $X^{2.11}$, $X^{2.12}$, $X^{2.13}$, $X^{2.14}$, $X^{2.15}$, $X^{2.16}$, $X^{2.17}$, $X^{2.18}$, $X^{2.19}$, $X^{2.20}$, $X^{2.21}$, $X^{2.22}$, $X^{2.23}$, $X^{2.24}$, $X^{2.25}$, $X^{2.26}$, $X^{2.27}$, $X^{2.28}$, $X^{2.29}$, $X^{2.30}$, $X^{2.31}$, $X^{2.32}$, $X^{2.33}$, $X^{2.34}$, $X^{2.35}$, $X^{2.36}$, $X^{2.37}$, $X^{2.38}$, $X^{2.39}$, $X^{2.40}$, $X^{2.41}$, $X^{2.42}$, respectively, wherein the definition of $R^2$ is assumed by $R^{2.1}$, $R^{2.2}$, $R^{2.3}$, $R^{2.4}$, $R^{2.5}$, $R^{2.6}$, $R^{2.7}$, $R^{2.8}$, $R^{2.9}$, $R^{2.10}$, $R^{2.11}$, $R^{2.12}$, $R^{2.13}$, $R^{2.14}$, $R^{2.15}$, $R^{2.16}$, $R^{2.17}$, $R^{2.18}$, $R^{2.19}$, $R^{2.20}$, $R^{2.21}$, $R^{2.22}$, $R^{2.23}$, $R^{2.24}$, $R^{2.25}$, $R^{2.26}$, $R^{2.27}$, $R^{2.28}$, $R^{2.29}$, $R^{2.30}$, $R^{2.31}$, $R^{2.32}$, $R^{2.33}$, $R^{2.34}$, $R^{2.35}$, $R^{2.36}$, $R^{2.37}$, $R^{2.38}$, $R^{2.39}$, $R^{2.40}$, $R^{2.41}$, $R^{2.42}$, the definition of $R^3$ is assumed by $R^{3.1}$, $R^{3.2}$, $R^{3.3}$, $R^{3.4}$, $R^{3.5}$, $R^{3.6}$, $R^{3.7}$, $R^{3.8}$, $R^{3.9}$, $R^{3.10}$, $R^{3.11}$, $R^{3.12}$, $R^{3.13}$, $R^{3.14}$, $R^{3.15}$, $R^{3.16}$, $R^{3.17}$, $R^{3.18}$, $R^{3.19}$, $R^{3.20}$, $R^{3.21}$, $R^{3.22}$, $R^{3.23}$, $R^{3.24}$, $R^{3.25}$, $R^{3.26}$, $R^{3.27}$, $R^{3.28}$, $R^{3.29}$, $R^{3.30}$, $R^{3.31}$, $R^{3.32}$, $R^{3.33}$, $R^{3.34}$, $R^{3.35}$, $R^{3.36}$, $R^{3.37}$, $R^{3.38}$, $R^{3.39}$, $R^{3.40}$, $R^{3.41}$, $R^{3.42}$, the definition of $R^4$ is assumed by $R^{4.1}$, $R^{4.2}$, $R^{4.3}$, $R^{4.4}$, $R^{4.5}$, $R^{4.6}$, $R^{4.7}$, $R^{4.8}$, $R^{4.9}$, $R^{4.10}$, $R^{4.11}$, $R^{4.12}$, $R^{4.13}$, $R^{4.14}$, $R^{4.15}$, $R^{4.16}$, $R^{4.17}$, $R^{4.18}$, $R^{4.19}$, $R^{4.20}$, $R^{4.21}$, $R^{4.22}$, $R^{4.23}$, $R^{4.24}$, $R^{4.25}$, $R^{4.26}$, $R^{4.27}$, $R^{4.28}$, $R^{4.29}$, $R^{4.30}$, $R^{4.31}$, $R^{4.32}$, $R^{4.33}$, $R^{4.34}$, $R^{4.35}$, $R^{4.36}$, $R^{4.37}$, $R^{4.38}$, $R^{4.39}$, $R^{4.40}$, $R^{4.41}$, $R^{4.42}$, the definition of $R^7$ is assumed by $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, the definition of $R^8$ is assumed by $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, the definition of $R^9$ is assumed by $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$, the definitions of $R^{20}$ to $R^{49}$ are assumed by R20.1 to $R^{49.1}$, $R^{20.2}$ to $R^{49.2}$, $R^{20.3}$ to $R^{49.3}$, $R^{20.4}$ to $R^{49.4}$, $R^{20.5}$ to $R^{49.5}$, $R^{20.6}$ to $R^{49.6}$, $R^{20.7}$ to $R^{49.7}$, $R^{20.8}$ to $R^{49.8}$, $R^{20.9}$ to $R^{49.9}$, $R^{20.10}$ to $R^{49.10}$, $R^{20.11}$ to $R^{49.11}$, $R^{20.12}$ to $R^{49.12}$, $R^{20.13}$ to $R^{49.13}$, $R^{20.14}$ to $R^{49.14}$, $R^{20.15}$ to $R^{49.15}$, $R^{20.16}$ to $R^{49.16}$, $R^{20.17}$ to $R^{49.17}$, $R^{20.18}$ to $R^{49.18}$, $R^{20.19}$ to $R^{49.19}$, $R^{20.20}$ to $R^{49.20}$, $R^{20.21}$ to $R^{49.21}$, $R^{20.22}$ to $R^{49.22}$, $R^{20.23}$ to $R^{49.23}$, $R^{20.24}$ to $R^{49.24}$, $R^{20.25}$ to $R^{49.25}$, $R^{20.26}$ to $R^{49.26}$, $R^{20.27}$ to $R^{49.27}$, $R^{20.28}$ to $R^{49.28}$, $R^{20.29}$ to $R^{49.29}$, $R^{20.30}$ to $R^{49.30}$, $R^{20.31}$ to $R^{49.31}$, $R^{20.32}$ to $R^{49.32}$, $R^{20.33}$ to $R^{49.33}$, $R^{20.34}$ to $R^{49.34}$, $R^{20.35}$ to $R^{49.35}$, $R^{20.36}$ to $R^{49.36}$, $R^{20.37}$ to $R^{49.37}$, $R^{20.38}$ to $R^{49.38}$, $R^{20.39}$ to $R^{49.39}$, $R^{20.40}$ to $R^{49.40}$, $R^{20.41}$ to $R^{49.41}$, $R^{20.42}$ to $R^{49.42}$, the definition of $X^1$ is assumed by $X^{1.1}$, $X^{1.2}$, $X^{1.3}$, $X^{1.4}$, $X^{1.5}$, $X^{1.6}$, $X^{1.7}$, $X^{1.8}$, $X^{1.9}$, $X^{1.10}$, $X^{1.11}$, $X^{1.12}$, $X^{1.13}$, $X^{1.14}$, $X^{1.15}$, $X^{1.16}$, $X^{1.17}$, $X^{1.18}$, $X^{1.19}$, $X^{1.20}$, $X^{1.21}$, $X^{1.22}$, $X^{1.23}$, $X^{1.24}$, $X^{1.25}$, $X^{1.26}$, $X^{1.27}$, $X^{1.28}$, $X^{1.29}$, $X^{1.30}$, $X^{1.31}$, $X^{1.32}$, $X^{1.33}$, $X^{1.34}$, $X^{1.35}$, $X^{1.36}$, $X^{1.37}$, $X^{1.38}$, $X^{1.39}$, $X^{1.40}$, $X^{1.41}$, $X^{1.42}$, the definition of $X^2$ is assumed by $X^2$, $X^{2.2}$, $X^{2.3}$, $X^{2.4}$, $X^{2.5}$, $X^{2.6}$, $X^{2.7}$, $X^{2.8}$, $X^{2.9}$, $X^{2.10}$, $X^{2.11}$, $X^{2.12}$, $X^{2.13}$, $X^{2.14}$, $X^{2.15}$, $X^{2.16}$, $X^{2.17}$, $X^{2.18}$, $X^{2.19}$, $X^{2.20}$, $X^{2.21}$, $X^{2.22}$, $X^{2.23}$, $X^{2.24}$, $X^{2.25}$, $X^{2.26}$, $X^{2.27}$, $X^{2.28}$, $X^{2.29}$, $X^{2.30}$, $X^{2.31}$, $X^{2.32}$, $X^{2.33}$, $X^{2.34}$, $X^{2.35}$, $X^{2.36}$, $X^{2.37}$, $X^{2.38}$, $X^{2.39}$, $X^{2.40}$, $X^{2.41}$, $X^{2.42}$.

The variables used within a definition of $R^2$, $R^3$, $R^4$, $R^7$, $R^8$, $R^9$, $R^{20}$ to $R^{49}$, $X^1$, $X^2$, and/or other variables that appear at multiple instances and are different may similarly be appropriately labeled to distinguish each group for greater clarity.

Further provided herein is a pharmaceutical composition including a pharmaceutically acceptable excipient and a compound, or pharmaceutically acceptable salt thereof, as described herein (e.g. a compound of formula (I) or (II), including embodiments thereof). In embodiments, the pharmaceutical composition includes a compound, or pharmaceutically acceptable salt thereof, as described herein (e.g. a compound of formula (I) or (II), including embodiments thereof) in a therapeutically effective amount. In embodiments, the pharmaceutical composition includes a second agent (e.g. therapeutic agent). In embodiments, the pharmaceutical composition includes a second agent (e.g. therapeutic agent) in a therapeutically effective amount. In embodiments, the second agent (e.g. therapeutic agent) is an anti-cancer agent. In embodiments, the second agent (e.g. therapeutic agent) is a chemotherapeutic.

II. METHODS OF TREATMENT

Also provided herein is a method of treating cancer in a subject in need thereof by administering an effective amount of a compound, or pharmaceutically acceptable salt thereof, as described herein, including embodiments thereof, to the subject. The compound may be administered as described herein, including embodiments, thereof. The method may include co-administering an effective amount of an anti-cancer agent as described herein. In embodiments, the anti-cancer agent is a chemotherapeutic agent.

The cancer may be, for example, lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, or prostate cancer. The method of treating cancer may be a method of treating lung cancer. The method of treating cancer may be a method of treating breast cancer. The method of treating cancer may be a method of treating ovarian cancer. The method of treating cancer may be a method of treating lymphoma. The method of treating cancer may be a method of treating pancreatic cancer. The method of treating cancer may be a method of treating melanoma. The method of treating cancer may be a method of treating prostate cancer. The method of treating cancer may be a method of treating sarcoma. The method of treating cancer may be a method of treating bladder cancer. The method of treating cancer may be a method of treating bone cancer. The method of treating cancer may be a method of treating brain cancer. The method of treating cancer may be a method of treating cervical cancer. The method of treating cancer may be a method of treating colon cancer. The method of treating cancer may be a method of treating esophageal cancer. The method of treating cancer may be a method of treating gastric cancer. The method of treating cancer may be a method of treating liver cancer. The method of treating cancer may be a method of treating head and neck cancer. The method of treating cancer may be a method of treating kidney cancer. The method of treating cancer may be a method of treating myeloma. The method of treating cancer may be a method of treating multiple myeloma. The method of treating cancer may be a method of treating thyroid cancer. In embodiments, the compounds set forth herein are provided as pharmaceutical compositions including the compound and a pharmaceutically acceptable excipient.

Also provided herein are methods of modulating the level, activity, or function of a protein associated with a disease (e.g. cancer). The method includes contacting the protein with an effective amount of a compound, or pharmaceutically acceptable salt thereof, as described herein, including embodiments thereof.

In embodiments, the method of modulation includes administering an effective amount of a compound, or pharmaceutically acceptable salt thereof, as described herein including embodiments thereof. In embodiments, the protein is selected from the group consisting of a JAK, JAK2, TYK2, c-Src, ABL1, T315I mutant ABL1, Aurora A, GSK-3β, CDK, a STAT, and STAT3. The protein may be a JAK. The protein may be Src. The protein may be GSK-3b. The protein may be a CDK. The protein may be STAT3. In embodiments, the method of modulation includes modulating different proteins (e.g. kinases). In embodiments, the method of modulation includes modulating two, three, four, five, or six proteins (e.g. kinases).

The method may include modulating the level (e.g. amount) of a protein associated with a disease (e.g. cancer). The method may include modulating the activity of a protein associated with a disease (e.g. cancer). The method may include modulating function of a protein associated with a disease (e.g. cancer). In embodiments, modulating is inhibiting and the compound, or pharmaceutically acceptable salt thereof, as described herein (including embodiments) is an inhibitor. In embodiments, the compounds set forth herein are provided as pharmaceutical compositions including the compound and a pharmaceutically acceptable excipient.

III. EMBODIMENTS

Embodiment P1 A Compound, or Pharmaceutically Acceptable Salt thereof, Having the Formula:

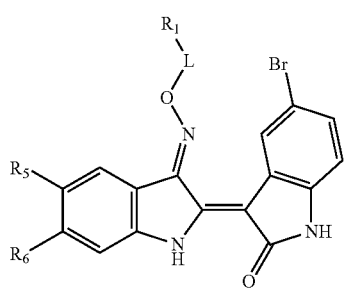

(I)

L is a bond or substituted or unsubstituted alkylene. $R^1$ is hydrogen, halogen, $-CX^1_3$, $-OCX^1_3$, $-CN$, $-OH$, $-NH_2$, $-C(O)OH$, $-C(O)OR^4$, $-CONH_2$, $-NO_2$, $-SH$, $-NHNH_2$, $-NR^2R^3$, $-OR^4$, $-SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^1$ is independently a halogen. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^2$ and $R^3$ are optionally joined together to form a substituted or unsubstituted heterocycloalkyl or substituted or unsubstituted heteroaryl. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ and $R^6$ are independently hydrogen, halogen, $-CX^2_3$, $-OCX^2_3$, $-CN$, $-OH$, $-NH_2$, $-C(O)OH$, $-C(O)OR^9$, $-CONH_2$, $-NO_2$, $-SH$, $-NHNH_2$, $-NR^7R^8$, $-OR^9$, $-SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$X^2$ is independently a halogen. $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^7$ and $R^8$ are optionally joined together to form a substituted or unsubstituted heterocycloalkyl or substituted or unsubstituted heteroaryl. and $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment P2 The compound of embodiment 1, wherein $R^5$ and $R^6$ are hydrogen.

Embodiment P3 The compound of any one of embodiments 1 to 2, wherein L is unsubstituted alkylene.

Embodiment P4 The compound of any one of embodiments 1 to 3, wherein L is unsubstituted $C_1$-$C_8$ alkylene.

Embodiment P5 The compound of any one of embodiments 1 to 4, wherein L is unsubstituted $C_1$-$C_4$ alkylene.

Embodiment P6 The compound of any one of embodiments 2 to 5, wherein L is unsubstituted $C_2$ alkylene.

Embodiment P7 The compound of embodiment 1, wherein L is a bond.

Embodiment P8 The compound of any one of embodiments 1 to 7, wherein $R^1$ is halogen, $-CX_3$, $-OCX_3$, $-CN$, $-OH$, $-NH_2$, $-C(O)OH$, $-C(O)OR^4$, $-CONH_2$, $-NO_2$, $-SH$, $-NHNH_2$, $-NR^2R^3$, $-OR^4$, $-SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment P9 The compound of any one of embodiments 1 to 8, wherein $R^1$ is $-NR^2R^3$.

Embodiment P10 The compound of any one of embodiments 1 to 9, wherein $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment P11 The compound of any one of embodiments 1 to 10, wherein $R^2$ and $R^3$ are independently substituted or unsubstituted alkyl.

Embodiment P12 The compound of any one of embodiments 1 to 11, wherein $R^2$ and $R^3$ are independently substituted or unsubstituted $C_1$-$C_8$ alkyl.

Embodiment P13 The compound of any one of embodiments 11 to 12, wherein $R^2$ and $R^3$ are independently substituted or unsubstituted $C_1$-$C_4$ alkyl.

Embodiment P14 The compound of any one of embodiments 1 to 13, wherein $R^2$ and $R^3$ are independently $-OH$ substituted or unsubstituted $C_1$-$C_4$ alkyl.

Embodiment P15 The compound of any one of embodiments 1 to 15, wherein $R^2$ and $R^3$ are independently unsubstituted $C_1$-$C_4$ alkyl.

Embodiment P16 The compound of any one of embodiments 1 to 9, wherein $R^2$ and $R^3$ are joined together to form a substituted or unsubstituted heterocycloalkyl or substituted or unsubstituted heteroaryl.

Embodiment P17 The compound of embodiment 16, wherein $R^2$ and $R^3$ are joined together to form a substituted or unsubstituted heterocycloalkyl.

Embodiment P18 The compound of any one of embodiments 16 to 17, wherein $R^2$ and $R^3$ are joined together to form a substituted or unsubstituted $C_5$-$C_7$ heterocycloalkyl.

Embodiment P19 The compound of any one of embodiments 16 to 19, wherein $R^2$ and $R^3$ are joined together to form a substituted $C_5$-$C_7$ heterocycloalkyl.

Embodiment P20 The compound of any one of embodiments 16 to 19, wherein $R^2$ and $R^3$ are joined together to form an $R^{23}$-substituted $C_5$-$C_7$ heterocycloalkyl, wherein $R^{23}$ is independently a substituted or unsubstituted alkyl or substituted or unsubstituted heteroalkyl.

Embodiment P21 The compound of embodiment 20, wherein $R^{23}$ is independently a substituted or unsubstituted $C_1$-$C_8$ alkyl or substituted or unsubstituted 2 to 8 membered heteroalkyl.

Embodiment P22 The compound of any one of embodiments 16 to 18, wherein $R^2$ and $R^3$ are joined together to form a substituted or unsubstituted pyrrolidinyl.

Embodiment P23 The compound of any one of embodiments 16 to 18, wherein $R^2$ and $R^3$ are joined together to form a substituted or unsubstituted piperazinyl.

Embodiment P24 The compound of any one of embodiments 1 to 23 comprising a protonated nitrogen cation.

Embodiment P25 The compound of any one of embodiments 1 to 24 comprising a plurality of protonated nitrogen cations.

Embodiment P26 A pharmaceutical composition comprising a pharmaceutically acceptable excipient and a compound of any one of embodiments 1 to 25.

Embodiment P27 A method of treating cancer in a subject in need thereof, the method comprising administering an effective amount of a compound of any one of embodiments 1 to 25.

Embodiment P28 The method of embodiment 27, wherein the compound is in a pharmaceutical composition comprising a pharmaceutically acceptable excipient.

Embodiment P29 The method of any one of embodiments 27 to 28, wherein the cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, or prostate cancer.

Embodiment P30 The method of any one of embodiments 27 to 29, comprising co-administering an effective amount of an anti-cancer agent.

Embodiment P31 A method of modulating a kinase, a JAK, JAK2, TYK2, Src, c-Src, ABL1, ABL1 T315I, an Aurora kinase, Aurora A, GSK-3b, a CDK, a STAT, or STAT3, the method comprising contacting the protein with the compound of any one of embodiments 1 to 25.

Embodiment P32 The method of embodiment 31, wherein the compound is in a pharmaceutical composition comprising a pharmaceutically acceptable excipient.

Embodiment P33 A method of modulating a Janus kinase, the method comprising contacting the Janus kinase with the compound of any one of embodiments 1 to 25.

Embodiment P34 The method of embodiment 33, wherein the compound is in a pharmaceutical composition comprising a pharmaceutically acceptable excipient.

Embodiment 1 A compound, or pharmaceutically acceptable salt thereof, having the formula:

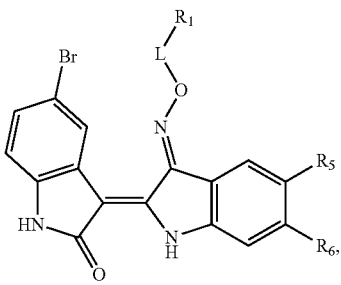

(I)

Wherein L is a bond or substituted or unsubstituted alkylene. $R^1$ is hydrogen, halogen, —$CX^1_3$, —$OCX^1_3$, —CN, —OH, —$NH_2$, —COOH, —C(O)$OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^1$ is independently a halogen. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^2$ and $R^3$ are optionally joined together to form a substituted or unsubstituted heterocycloalkyl or substituted or unsubstituted heteroaryl. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ and $R^6$ are independently hydrogen, halogen, —$CX^2_3$, —$OCX^2_3$, —CN, —OH, —$NH_2$, —COOH, —C(O)$OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^2$ is independently a halogen. $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^7$ and $R^8$ are optionally joined together to form a substituted or unsubstituted heterocycloalkyl or substituted or unsubstituted heteroaryl. $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 2 The compound of embodiment 1, wherein $R^5$ and $R^6$ are hydrogen.

Embodiment 3 The compound of any one of embodiments 1 to 2, wherein L is unsubstituted alkylene.

Embodiment 4 The compound of any one of embodiments 1 to 3, wherein L is unsubstituted $C_1$-$C_8$ alkylene.

Embodiment 5 The compound of any one of embodiments 1 to 4, wherein L is unsubstituted $C_1$-$C_4$ alkylene.

Embodiment 6 The compound of any one of embodiments 1 to 5, wherein L is unsubstituted $C_2$ alkylene.

Embodiment 7 The compound of embodiments 1 to 6, wherein L is a bond.

Embodiment 8 The compound of any one of embodiments 1 to 7, wherein $R^1$ is halogen, —$CX_3$, —$OCX_3$, —CN, —OH, —NH₂, —COOH, —C(O)OR⁴, —CONH₂, —NO₂, —SH, —NHNH₂, —NR²R³, —SR⁴, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 9 The compound of any one of embodiments) to 8, wherein R¹ is —NR²R³.

Embodiment 10 The compound of any one of embodiments 1 to 9, wherein R² and R³ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 11 The compound of any one of embodiments 1 to 10, wherein R² and R³ are independently substituted or unsubstituted alkyl.

Embodiment 12 The compound of any one of embodiments 1 to 11, wherein R² and R³ are independently substituted or unsubstituted $C_1$-$C_8$ alkyl.

Embodiment 13 The compound of any one of embodiments 1 to 12, wherein R² and R³ are independently substituted or unsubstituted $C_1$-$C_4$ alkyl.

Embodiment 14 The compound of any one of embodiments 1 to 13, wherein R² and R³ are independently —OH substituted or unsubstituted $C_1$-$C_4$ alkyl.

Embodiment 15 The compound of any one of embodiments 1 to 14, wherein R² and R³ are independently unsubstituted $C_1$-$C_4$ alkyl.

Embodiment 16 The compound of any one of embodiments 1 to 15, wherein R² and R³ are joined together to form a substituted or unsubstituted heterocycloalkyl or substituted or unsubstituted heteroaryl.

Embodiment 17 The compound of embodiments 1 to 16, wherein R² and R³ are joined together to form a substituted or unsubstituted heterocycloalkyl.

Embodiment 18 The compound of embodiments 1 to 17, wherein R² and R³ are joined together to form a substituted or unsubstituted $C_5$-$C_7$ heterocycloalkyl.

Embodiment 19 The compound of any one of embodiments 1 to 16, wherein R² and R³ are joined together to form a substituted $C_5$-$C_7$ heterocycloalkyl.

Embodiment 20 The compound of any one of embodiments 1 to 16, wherein R² and R³ are joined together to form an R²³-substituted $C_5$-$C_7$ heterocycloalkyl, wherein R²³ is independently a substituted or unsubstituted alkyl or substituted or unsubstituted heteroalkyl.

Embodiment 21 The compound of embodiment 20, wherein R²³ is independently a substituted or unsubstituted $C_1$-$C_8$ alkyl or substituted or unsubstituted 2 to 8 membered heteroalkyl.

Embodiment 22 The compound of embodiments 1 to 16, wherein R² and R³ are joined together to form a substituted or unsubstituted pyrrolidinyl.

Embodiment 23 The compound of embodiments 1 to 16, wherein R² and R³ are joined together to form a substituted or unsubstituted piperazinyl.

Embodiment 24 The compound of embodiments 1 to 23 comprising a protonated nitrogen cation.

Embodiment 25 The compound of embodiments 1 to 24 comprising a plurality of protonated nitrogen cations.

Embodiment 26 The compound of embodiment 1 having formula:

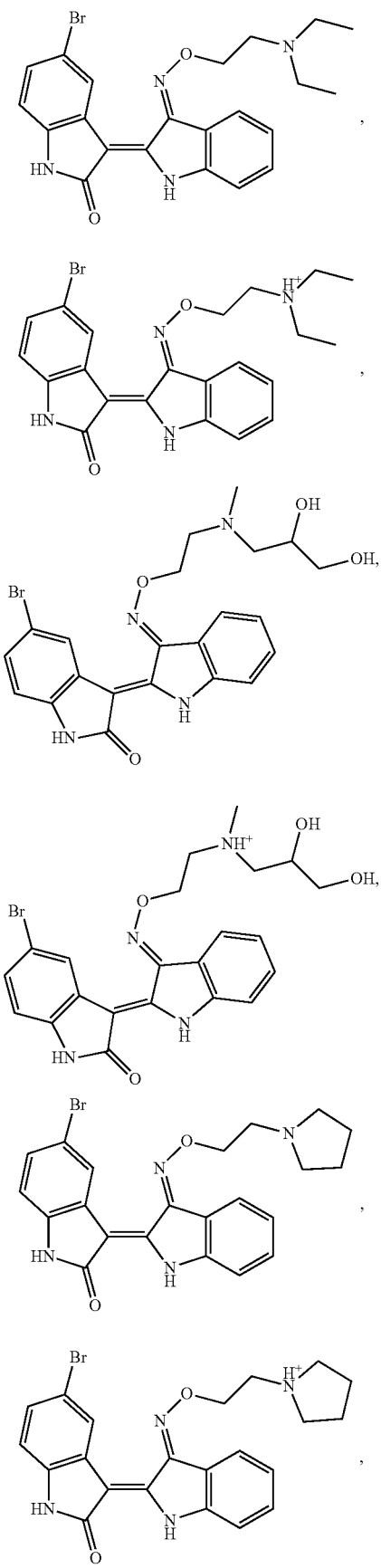

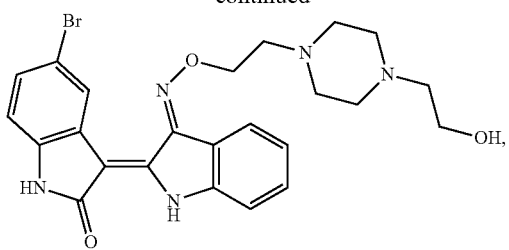
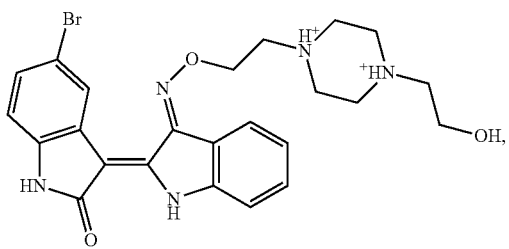
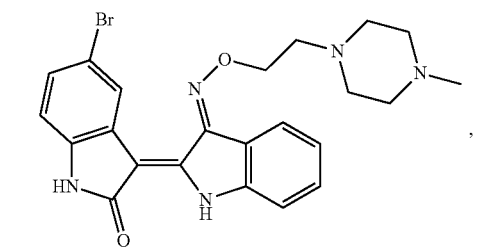
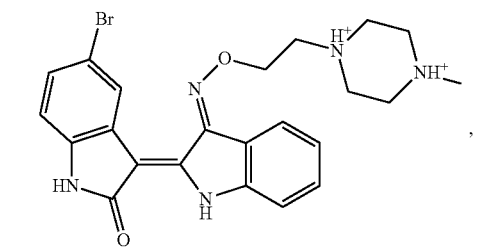
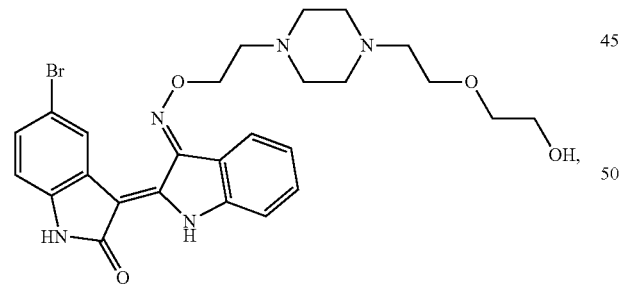
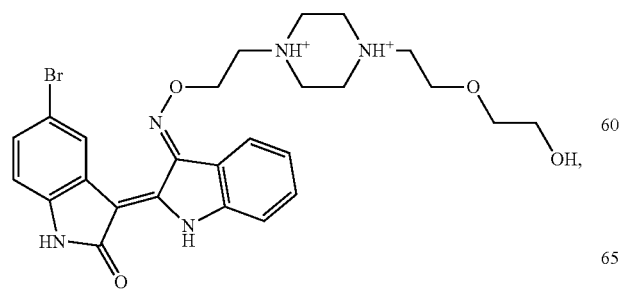
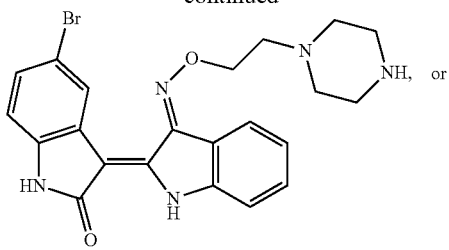
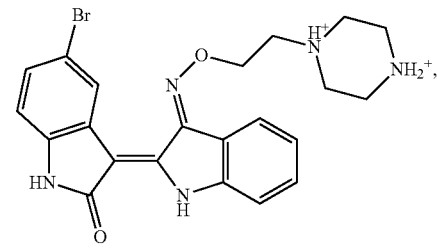
including pharmaceutical salts thereof.
Embodiment 27 The compound of embodiments 1 having formula:
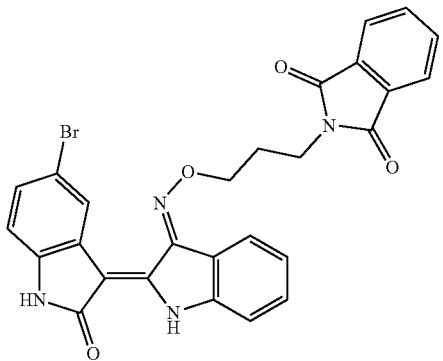
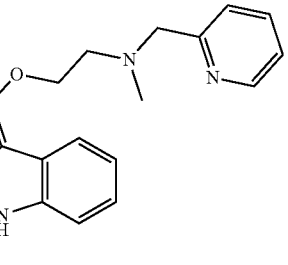
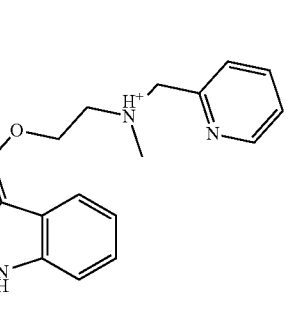

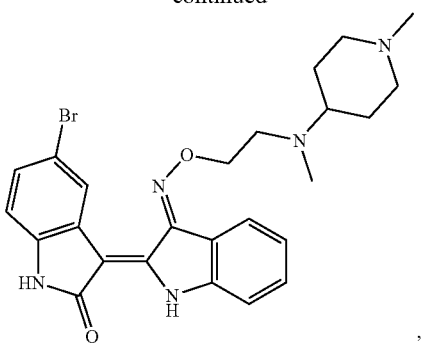

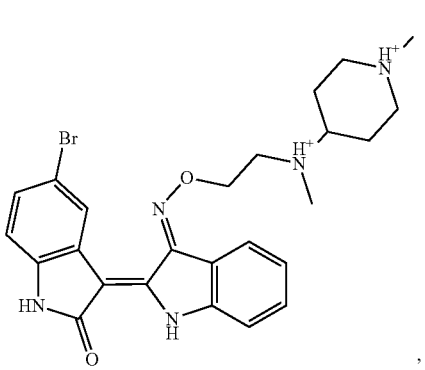

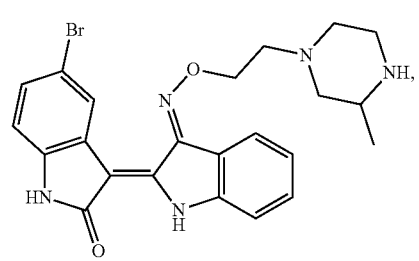

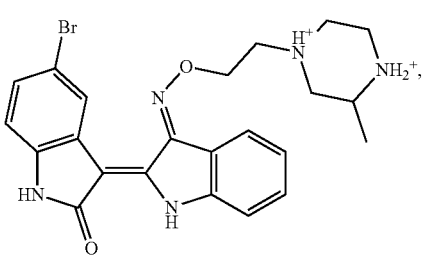

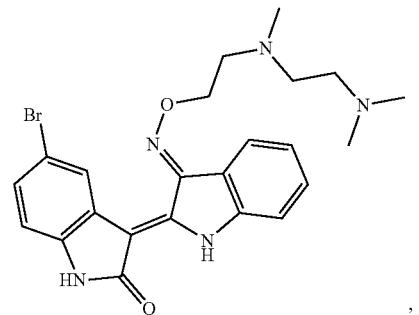

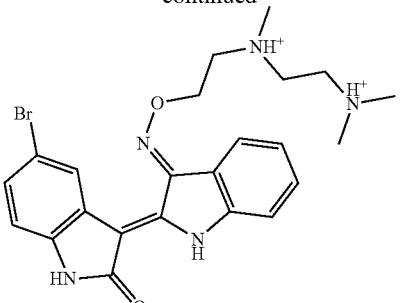

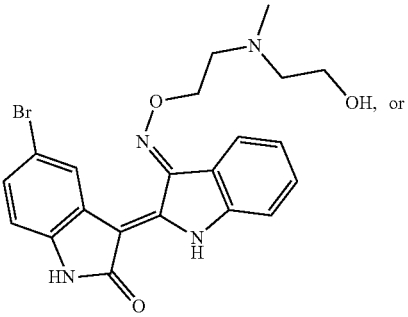

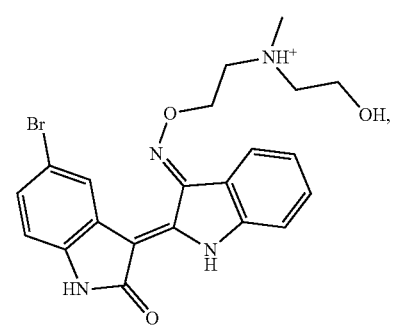 [SMILES: C[NH+](CCO)CCO/N=C1/C(=C2/C(=O)Nc3ccc(Br)cc32)Nc2ccccc21]

including pharmaceutical salts thereof.

Embodiment 28 A pharmaceutical composition comprising a pharmaceutically acceptable excipient and a compound of embodiments 1 to 27.

Embodiment 29 The compound of embodiments 1 to 28 for use in treating cancer in a subject in need thereof.

Embodiment 30 The compound of embodiment 29, wherein the compound is administered in an effective amount to the subject.

Embodiment 31 The compound of embodiments 29 to 30, wherein the compound is in a pharmaceutical composition comprising a pharmaceutically acceptable excipient.

Embodiment 32 The compound of embodiments 29 to 31, wherein the cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, or prostate cancer.

Embodiment 33 The compound of embodiments 29 to 32, wherein the compound is co-administered with an effective amount of an anti-cancer agent.

Embodiment 34 A method of modulating a kinase, a JAK, JAK2, TYK2, Src, c-Src, ABL1, ABL1 T315I, an Aurora kinase, Aurora A, GSK-3b, a CDK, a STAT, or STAT3, the method comprising contacting the protein with the compound embodiments 1 to 28.

Embodiment 35 The method of embodiment 34, wherein the compound is in a pharmaceutical composition comprising a pharmaceutically acceptable excipient.

Embodiment 36 A method of modulating a Janus kinase, the method comprising contacting the Janus kinase with the compound embodiments 1 to 28.

Embodiment 37 The method of embodiment 36, wherein the compound is in a pharmaceutical composition comprising a pharmaceutically acceptable excipient.

IV. EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

TABLE 1

Determination of $IC_{50}$ values of 5BIODs using solid and blood tumor cells. MTS assays were performed for cell viability as described for FIGS. 2A-2G. Each experiment was performed in quadruplicate. $IC_{50}$ values (μM) of 5-bromo indirubins against cancer cells.

| Comp. ID | A549 lung | MDA-MB-231 breast | SKOV3 ovarian | A2058 melanoma | DU145 prostate | PaCa2 pancreatic | T315l Alb mutant KCL-22 CML |
|---|---|---|---|---|---|---|---|
| 1276 | 0.47 | 0.30 | 0.41 | 0.36 | 0.42 | 1.2 | 0.30 |
| 1277 | *ND | ND | ND | 1.9 | 0.77 | ND | ND |
| 1278 | 0.60 | 0.71 | 0.75 | 1.7 | 0.78 | 2.5 | 0.5 |
| 1279 | ND | ND | ND | 2.2 | 2.0 | ND | ND |
| 1280 | 0.84 | 0.66 | 1.34 | 1.6 | 0.66 | 0.96 | 0.86 |
| 1281 | 0.40 | 0.37 | 0.75 | 1.8 | 0.66 | 0.44 | 0.58 |
| 1282 | 0.50 | 0.78 | 0.77 | ND | 0.91 | 1 | ND |
| 1283 | ND | ND | ND | ND | 2.1 | ND | ND |
| 1284 | 0.44 | 1.0 | 1.36 | ND | ND | ND | ND |
| 1285 | ND | ND | ND | ND | ND | ND | ND |
| 1286 | 0.93 | 1.36 | 1.84 | ND | ND | ND | ND |
| 1287 | ND | ND | ND | ND | ND | ND | ND |
| 1226 | ND | ND | ND | ND | 3.0 | ND | ND |
| 1289 | 0.38 | 0.40 | 0.46 | 1.1 | 0.69 | 0.46 | 0.6 |
| 1501 | ND | ND | ND | 0.88 | 0.32 | ND | ND |
| 1502 | ND | ND | ND | 1.7 | 1.5 | ND | ND |

*ND: not determined

Example 2

TABLE 2

5BIODs inhibit activities of Src and Janus kinases (JAKs) in vitro. $IC_{50}$ values (nM) against kinase activities in vitro using recombinant proteins

| Kinase | 1276 | 1277 | 1278 | 1279 | 1281 | 1226 | 1289 |
|---|---|---|---|---|---|---|---|
| ABL1 | 1020 | 4770 | 392 | 1440 | 2500 | 432 | 71.4 |
| ABL1 (T315I) | 6580 | >10000 | 1550 | 5550 | 7080 | 1480 | 214 |
| AuroraA | 954 | 3310 | 122 | 301 | 2050 | 366 | 143 |
| c-Src | 34.3 | 95.4 | 12.1 | 69.6 | 19.7 | 18.2 | 3.7 |
| JAK2 | 526 | 1250 | 104 | 410 | 264.0 | 274 | 47.6 |
| TYK2 | 31.6 | 146 | 27 | 62.7 | 21.0 | 138 | 20.1 |

The kinase assays were performed with recombinant proteins. Briefly, proteins, freshly prepared substrates and $^{33}$P-ATP (specific activity 0.01 μCi/μl final) were mixed in reaction buffer (20 mM HEPES pH 7.5, 10 mM $MgCl_2$, 1 mM EGTA, 0.02% Brij35, 0.02 mg/ml BSA, 0.1 mM $Na_3VO_4$, 2 mM DTT) in the presence of DMSO as control or 5BIODs. The mixtures were reacted for 120 min at room temperature. Samples were transferred onto P81 ion exchange paper and filters were extensively washed with 0.75% phosphoric acid. The radioactivities were monitored.

Example 3

General Procedure for the Preparation of 5-bromo-indirubin

Commercially available 5-bromo-isatin (1 eq.) and 3-acetoxyindole (0.8 eq.) were dissolved in methanol in presence of sodium carbonate. The mixture was stirred for about 3.5 h. After addition of methanolic water (1/1) the precipitate was filtered, washed with water and dried to afford the 5-bromoindirubin with ~80% yield.

$^1$H NMR (DMSO-d6, 400 MHz, δ ppm, J in Hz): 11.12 (2H, s, N—H, N'—H), 8.94 (1H, s, H-4), 7.66 (1H, d, J=7.5 Hz, H-4'), 7.60 (1H, t, J=7.5 Hz, H-6'), 7.45 (2H, m, H-6, 7'), 7.05 (1H, t, J=7.5 Hz, H-5'), 6.86 (1H, d, J=8.3 Hz, H-7). MS (m/z, ESI+): m/z: 341, 343 (M+H)+.

General Procedure for the Preparation of 5-bromo-3'-oxim-indirubin 5-bromoindirubin (1 eq) is then dissolved in pyridine in presence of an excess of hydroxylamine hydrochloride (10 eq) and refluxed for 1 h30. Addition of water after cooling, filtration and washings with water afforded the 5-bromo-3'-oxim-indirubin (5-BIO) in quantitative yield.

$^1$H NMR (DMSO-d6, 400 MHz, δ ppm, J in Hz): 13.71 (1H, brs, NOH), 11.85 (1H, s, N'—H), 10.84 (1H, s, N—H), 8.76 (1H, brs, H-4), 8.24 (1H, d, J=7.7 Hz, H-4'), 7.42 (2H, m, H-6', 7'), 7.26 (1H, m, H-6), 7.06 (1H, t, J=7.7 Hz, H-5'), 6.84 (1H, d, J=8.2 Hz, H-7). MS (m/z, ESI+): 356, 358 (M+H)+.

General Procedure for the Preparation of 5-bromoindirubin-3'-(O-bromoethyl)oxime To a solution of 5-BIO (1eq) in DMF were added triethylamine and dibromoethane (2 eq). The reaction is stirred for 24 h at room temperature. Then water is added and the precipitate was filtered and washed with water to afford the 5-bromoindirubin-3'-(O-bromoethyl)-oxime.

$^1$H NMR (DMSO-d6, 400 MHz, δ ppm, J in Hz): 11.72 (1H, s, N'—H), 10.94 (1H, s, N—H), 8.80 (1H, d, J=1.9 Hz, H-4), 8.21 (1H, d, J=7.5 Hz, H-4'), 7.47 (2H, m, H-6', 7'), 7.32 (1H, dd, J=8.0, 1.9 Hz, H-6), 7.08 (1H, m, H-5'), 6.87 (1H, d, J=8.0 Hz, H-7), 4.89 (2H, t, J=5.6 Hz, H-1"), 4.03 (2H, t, J=5.6 Hz, H-2"). MS (m/z, ESI+): 463, 465, 467 (M+H)+.

General Procedure for the Preparation of the 5-bromoindirubin-3'-(O-ethylamine)oxime 5-bromoindirubin-3'-(O-bromoethyl)oxime was dissolved in anhydrous DMF. An excess of the appropriate amine (diethylamine, piperazine, N-methylpiperazine, 3-methylamine-1,2-propanediol, 1-(2-hydroxyethyl)piperazine and 1-[2-(2-hydroxyethoxy)-ethyl]piperazine) was added and the mixture was heated at 90° C. in CEM Single-Mode microwave (100 W) for about 40 min. Water was added, the precipitate filtered and washed with water and cyclohexane affording the corresponding derivatives in 80-90% yield.

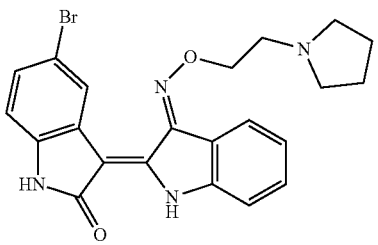

1280

$^1$H NMR (DMSO-d6, 400 MHz, δ ppm, J in Hz): 11.75 (1H, s, N'—H), 10.92 (1H, s, N—H), 8.86 (1H, d, J=2.0 Hz, H-4), 8.16 (1H, d, J=7.6 Hz, H-4'), 7.46 (2H, m, H-6', 7'), 7.30 (1H, d, J=8.2 Hz, H-6), 7.07 (1H, m, H-5'), 6.86 (1H, d, J=8.2 Hz, H-7), 4.70 (2H, t, J=5.8 Hz, H-1"), 3.04 (2H, t, J=5.8 Hz, H-2"), 2.60 (4H, m, H-2''', 5'''), 1.68 (4H, m, H-3'''', 4''''). MS (m/z, ESI+): 453, 455 (M+H)+.

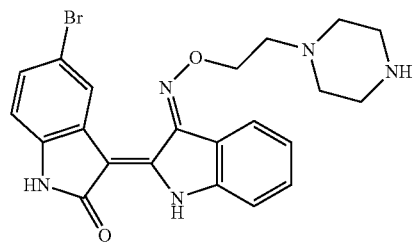

1288

$^1$H NMR (DMSO-d6, 400 MHz, δ_ppm, J in Hz): 11.73 (1H, s, N'—H), 10.90 (1H, s, N—H), 8.88 (1H, d, J=2.0 Hz, H-4), 8.14 (1H, d, J=7.6 Hz, H-4'), 7.45 (2H, m, H-6', 7'), 7.30 (1H, d, J=8.2 Hz, H-6), 7.07 (1H, m, H-5'), 6.86 (1H, d, J=8.2 Hz, H-7), 4.70 (2H, t, J=5.8 Hz, H-1"), 2.85 (2H, t, J=5.8 Hz, H-2"), 2.69 (4H, m, H-2''', 5'''), 2.49 (4H, m, H-3''', 4'''). MS (m/z, ESI+): 453, 455 (M+H)+.

General Procedure for the Preparation of the 5-bromoindirubin-3'-(O-ethylamine)oxime salt Each amino derivative was then dissolved in anhydrous THF and a 2 M HCl-Et$_2$O solution is added dropwise until no more precipitation is observed affording the corresponding chloride salt.

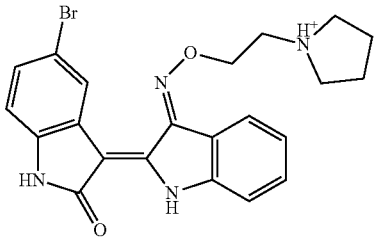

1281

$^1$H NMR (DMSO-d6, 400 MHz, δ_ppm, J in Hz): 11.75 (1H, s, N'—H), 10.97 (1H, s, N—H), 9.92 (1H, brs, H-1'''), 8.79 (1H, d, J=2.0 Hz, H-4), 8.24 (1H, dd, J=7.8, 0.8 Hz, H-4'), 7.49 (2H, m, H-6', 7'), 7.33 (1H, dd, J=8.0, 2.0 Hz, H-6), 7.09 (1H, m, H-5'), 6.88 (1H, d, J=8.0 Hz, H-7), 4.91

(2H, m, H-1''), 3.86 (2H, m, H-2''), 3.67 (2H, m, H-2'''a, 5'''a), 3.16 (2H, m, 2'''b, 5'''b), 2.03 (2H, m, H-3'''a, 4'''a), 1.86 (2H, m, H-3'''b, 4'''b).

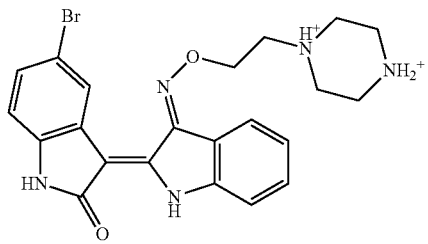

1289

¹H NMR (DMSO-d6, 400 MHz, δ ppm, J in Hz): 11.82 (1H, s, N'—H), 11.05 (1H, s, N—H), 9.32 (2H, br, H-1''', 4'''), 8.79 (1H, d, J=2.0 Hz, H-4), 8.25 (1H, d, J=7.5 Hz, H-4'), 7.48 (2H, m, H-6', 7'), 7.35 (1H, dd, J=8.0, 2.0 Hz, H-6), 7.06 (1H, ddd, J=7.5, 4.1, 1.4 Hz, H-5'), 6.89 (1H, d, J=8.0 Hz, H-7), 4.98 (2H, m, H-1''), 3.70 (2H, m, H-2''), 3.50 (8H, overlapped, H-2''', 3''', 5''', 6''').

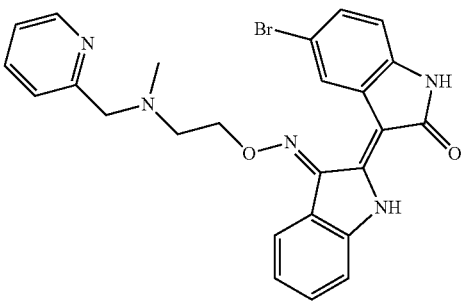

XNH6

¹H NMR (400 MHz, CDCl₃) δ11.72 (b, 1H), 10.88 (b, 1H), 8.78 (s, 1H), 8.38 (d, J=4.8 Hz, 1H), 8.13 (d, J=7.4 Hz, 1H), 7.58-7.36 (m, 4H), 7.27 (d, J=2.0 Hz, 8.2 Hz, 1H), 7.20-7.10 (m, 1H), 7.10-7.01 (m, 1H), 6.83 (d, J=8.2 Hz, 1H), 4.72 (t, J=5.8 Hz, 2H), 3.80-3.70 (m, 2H), 3.10-2.96 (m, 2H), 2.35 (s, 3H); ¹³C NMR (100 MHz, CDCl₃) δ170.9, 151.8, 149.1, 145.8, 145.4, 138.0, 136.7, 133.5, 128.8, 128.6, 125.7, 124.9, 123.0, 122.5, 122.3, 116.6, 112.9, 112.6, 111.0, 99.3, 75.1, 63.8, 55.9, 42.9; HRMS $C_{25}H_{22}BrN_5O_2$ [M+H]⁺ calc'd 504.1030, found. 504.1039.

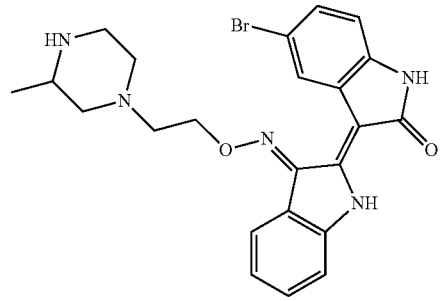

XNH9

¹H NMR (400 MHz, CDCl₃) δ11.72 (b, 1H), 10.89 (b, 1H), 8.83 (d, J=2.0 Hz, 1H), 8.15 (d, J=7.4 Hz, 1H), 7.48-7.40 (m, 2H), 7.28 (dd, J=2.0, 8.2 Hz, 1H), 7.09-7.00 (m, 1H), 6.84 (d, J=8.2 Hz, 1H), 4.69 (t, J=5.8 Hz, 2H), 3.40-3.30 (m, 4H), 2.87 (t, J=5.6 Hz, 2H), 2.85-2.70 (m, 3H), 2.70-2.60 (m, 2H), 2.10-2.00 (m, 1H), 1.72 (t, J=10.2 Hz, 1H), 0.87 (d, J=6.2 Hz, 3H); ¹³C NMR (100 MHz, CDCl₃) δ170.9, 151.8, 145.8, 145.4, 138.0, 133.4, 128.7, 128.7, 125.7, 124.9, 122.3, 116.6, 112.9, 112.6, 111.0, 99.2, 74.9, 61.6, 57.3, 53.9, 50.6, 45.7, 19.9; HRMS $C_{23}H_{24}BrN_5O_2$ [M+H]⁺ calc'd 482.1186, found. 482.1183.

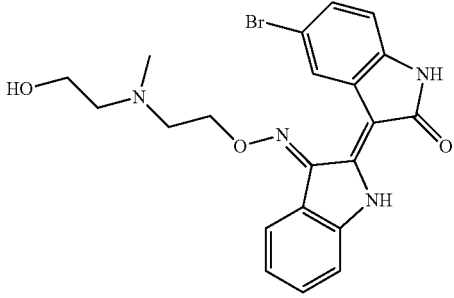

XNH12

¹H NMR (400 MHz, CDCl₃) δ11.73 (b, 1H), 10.89 (b, 1H), 8.83 (d, J=2.0 Hz, 1H), 8.15 (d, J=7.8 Hz, 1H), 7.48-7.40 (m, 2H), 7.28 (dd, J=2.0, 8.2 Hz, 1H), 7.09-7.01 (m, 1H), 6.84 (d, J=8.2 Hz, 1H), 4.67 (t, J=5.6 Hz, 2H), 4.34 (t, J=5.2 Hz, 1H), 3.46 (dd, J=6.2, 11.8 Hz, 1H), 2.99 (t, J=5.8 Hz, 2H), 2.54 (t, J=6.2 Hz, 2H), 2.3 (s, 3H); ¹³C NMR (100 MHz, CDCl₃) δ170.9, 151.8, 145.8, 145.4, 138.0, 133.4, 128.8, 128.6, 125.7, 124.9, 122.4, 116.6, 112.9, 112.5, 111.0, 99.2, 75.4, 60.2, 59.5, 56.5, 43.3; HRMS $C_{21}H_{21}BrN_4O_3$ [M+H]⁺ calc'd 457.0870, found. 457.0863.

Example 4

Figure 5:
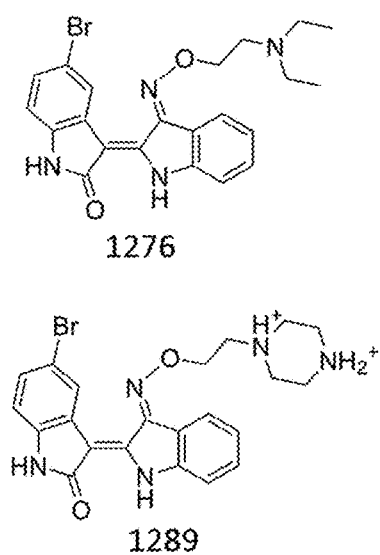
FIG. 5. Kinase profiling in vitro for compounds #1276 and #1289.
Figure 6:
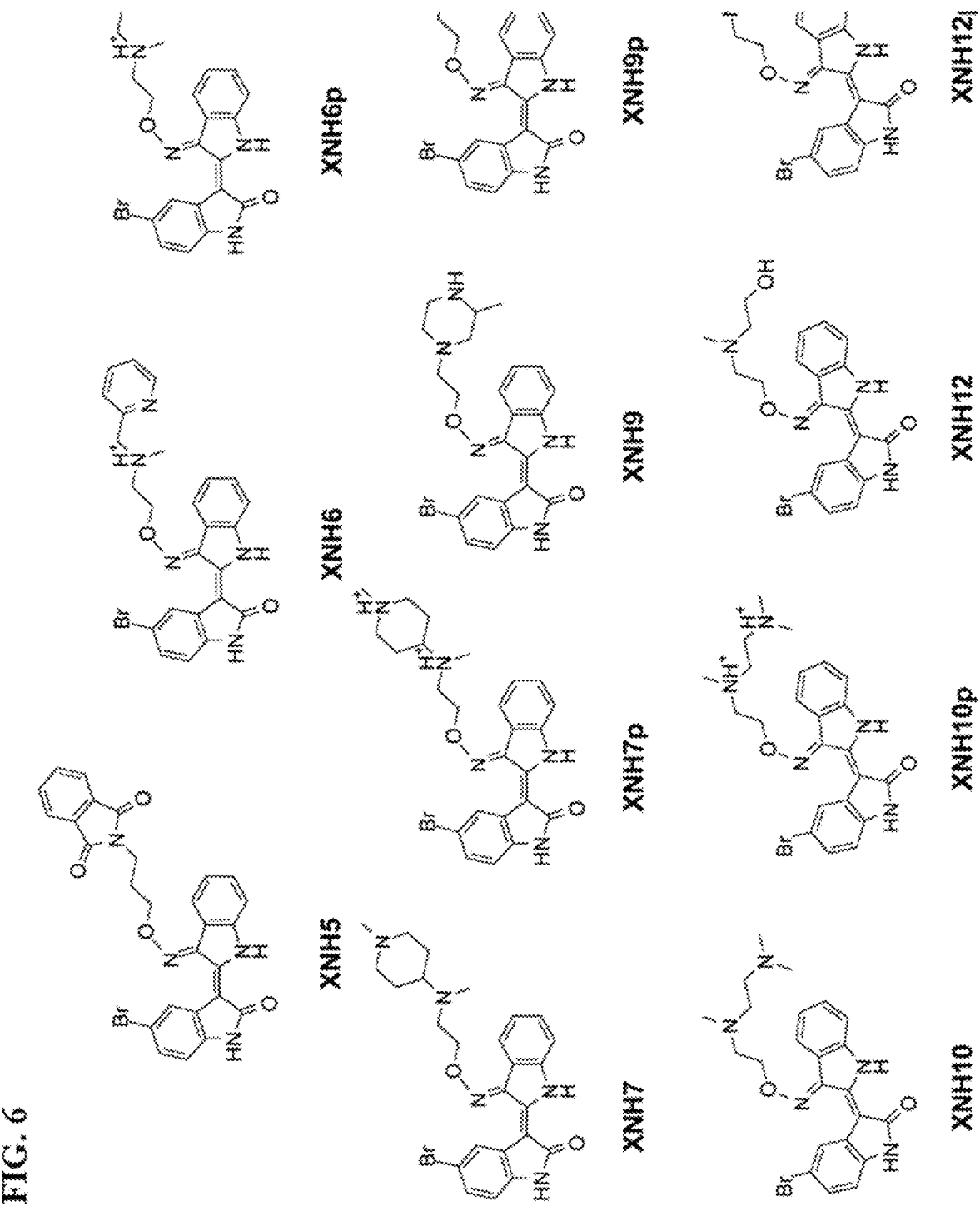
FIG. 6. Structures of 5-bromoindirubin-3'-oxime derivatives (5BIODs).

Kinase profiling in vitro for 1276 and 1289. See FIG. 5. The kinase assays were performed with recombinant proteins. Briefly, proteins, freshly prepared substrates and ³³P-ATP (specific activity 0.01 μCi/μl final) were mixed in reaction buffer (20 mM HEPES pH 7.5, 10 mM MgCl₂, 1 mM EGTA, 0.02% Brij35, 0.02 mg/ml BSA, 0.1 mM Na₃VO₄, 2 mM DTT) in the presence of DMSO as control, 1276 or 1289. The mixtures were reacted for 120 min at room temperature. Samples were transferred onto P81 ion exchange paper and filters were extensively washed with 0.75% phosphoric acid. The radioactivities were monitored. IC₅₀ values were determined using GraphPad Prism software.

Figure 7A:
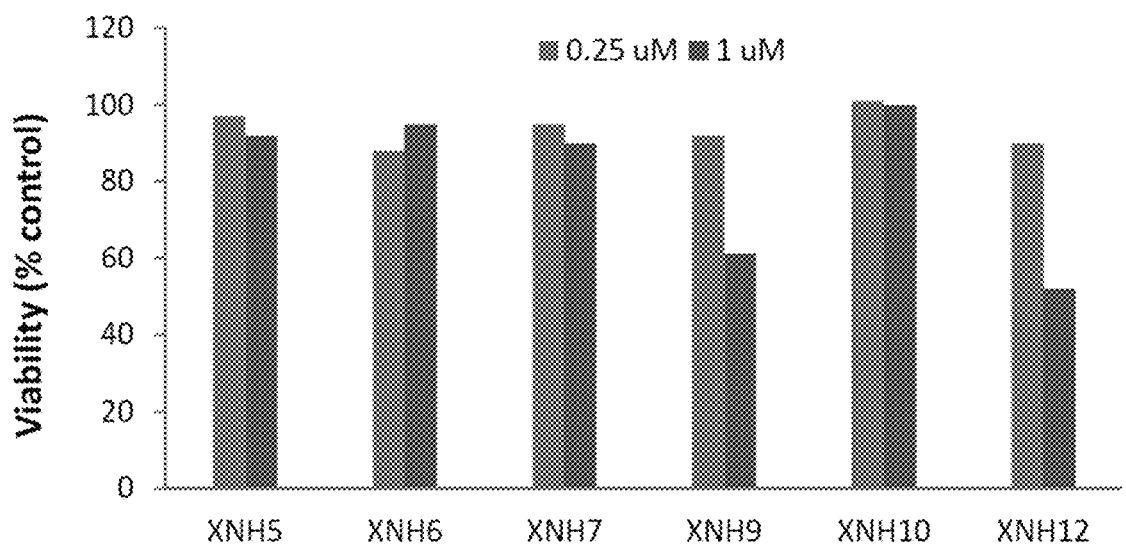
FIGS. 7A-7B. Effects of compounds described herein on viabilities of human cancer cells.
Figure 7B:
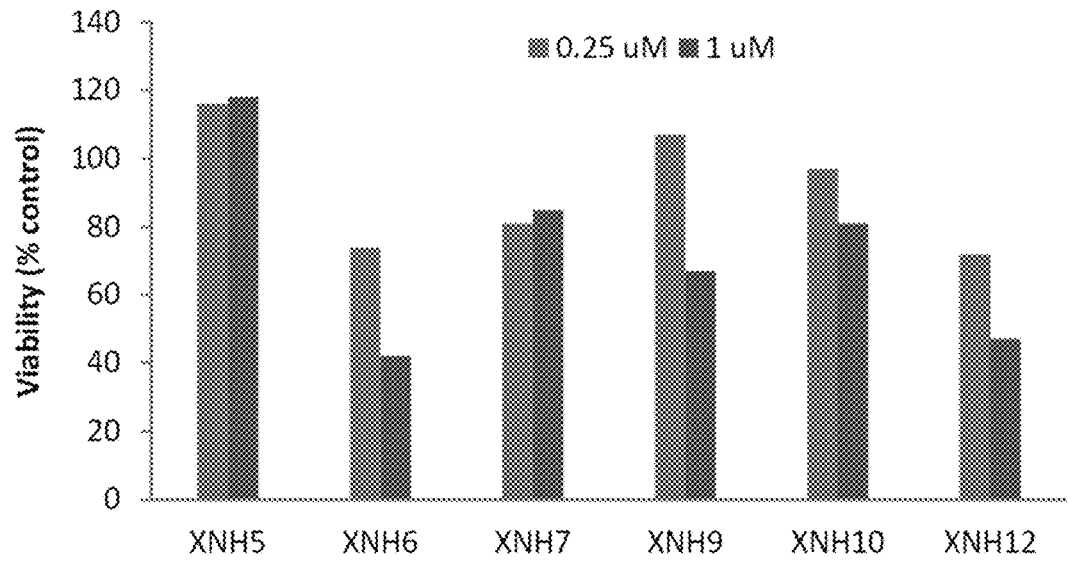
Figure 8A:
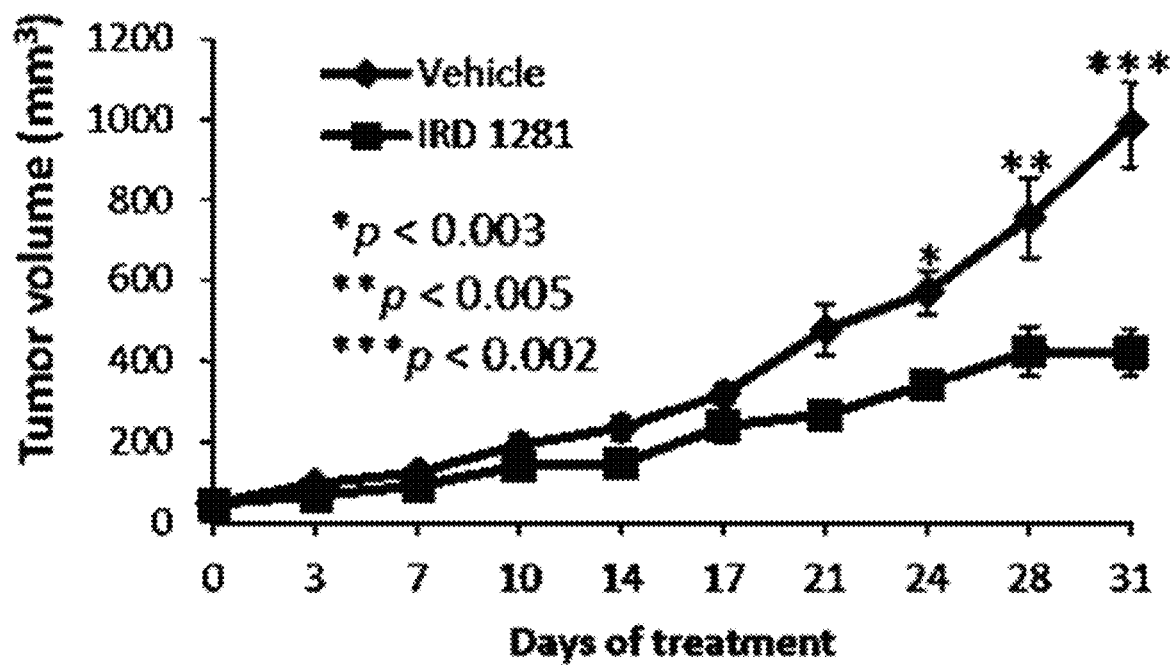
FIGS. 8A-8D: Efficacy of compounds 1281.
Figure 8B:
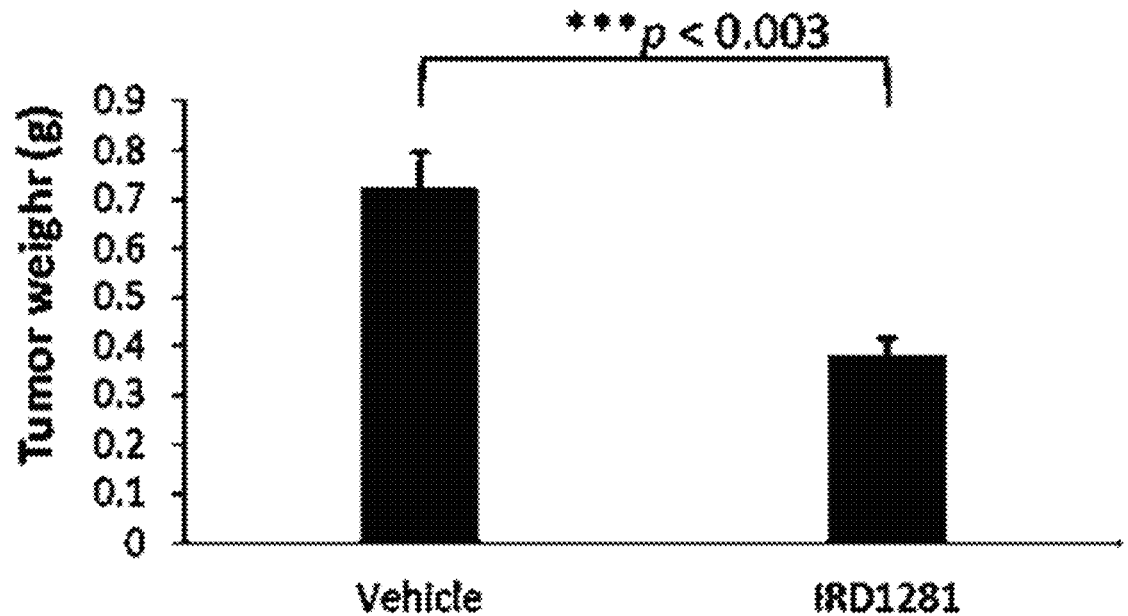
Figure 8C:
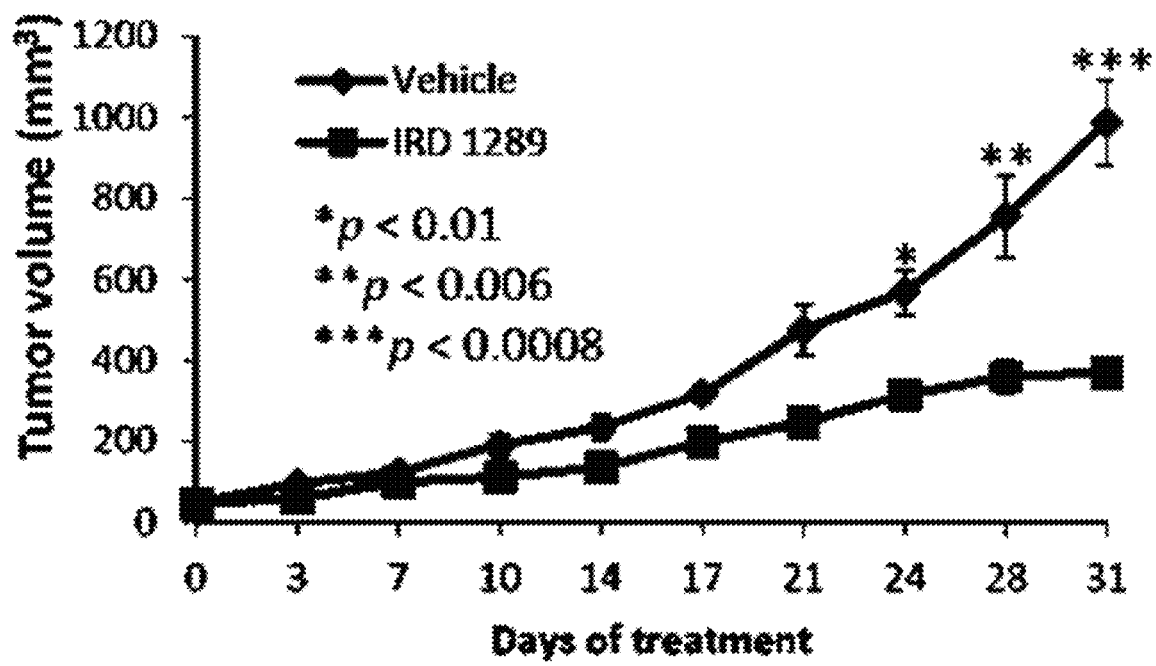
Figure 8D:
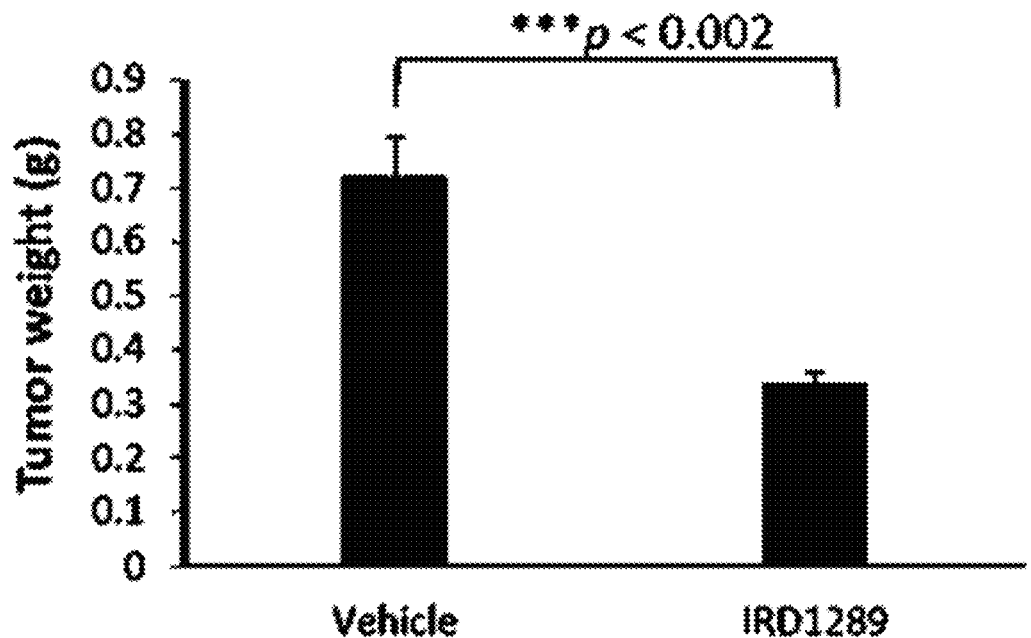

MTS assays were performed for cell viability. See FIGS. 7A-7B. Human A2058 melanoma (FIG. 7A) and DU145 prostate cancer (FIG. 7B) cancer cells (5000/well) were seeded in 96-well plates, incubated overnight at 37° C. in 5% (v/v) CO₂ and exposed to XNHs at 0.25 uM or 1 uM concentration for 48 h. DMSO was used as the vehicle control. Cell viability was determined by tetrazolium conversion to its formazan dye and absorbance was measured at 490 nm using an automated ELISA plate reader and each experiment was performed in quadruplicate.

Human A549 non-small cell lung cancer cells (5×10⁶) were resuspended in serum-free RPMI1640 medium and subcutaneously injected into the flank of 5-6 weeks old NOD/SCID/IL-2 rg(ko)(NSG) female mouse. See FIGS. 8A-8D. When palpable tumor sizes reached at approximately 70 mm³, mice were divided into two groups (vehicle=10, treatment=10). Then, 1281 (left panel) or 1289 (right panel) was administered with oral administration injection at 25 mg/kg with vehicle (10% DMSO+30% Solutol+60% Saline), twice daily for 31 days. Tumor volumes were calculated by the formula $1/2a \times b^2$, where a is the long diameter, and b is the short diameter. Tumor volumes correlate with tumor weights. The statistical significance of group differences was analyzed using a Student's t-test with the two-tailed distribution. P values less than 0.05 were considered statistically significant.

What is claimed is:

1. A method of treating cancer in a subject in need thereof, the method comprising administering to the subject a therapeutically effective amount of a compound

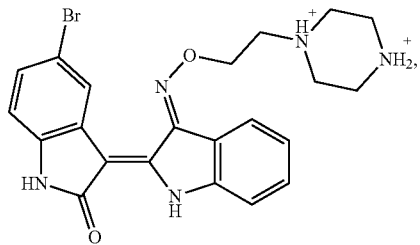

(1289)

or a pharmaceutically acceptable salt thereof; and
wherein said cancer is lung cancer, breast cancer, ovarian cancer, leukemia, melanoma, pancreatic cancer, or prostate cancer.

2. The method of claim 1, wherein said compound is in a pharmaceutical composition comprising a pharmaceutically acceptable excipient.

3. The method of claim 1, wherein said compound is co-administered with an effective amount of an anti-cancer agent.

* * * * *